United States Patent
Beyer et al.

(10) Patent No.: US 10,029,109 B2
(45) Date of Patent: Jul. 24, 2018

(54) DEFIBRILLATOR

(71) Applicant: Revive Solutions, Inc., San Mateo, CA (US)

(72) Inventors: Rory M. Beyer, San Mateo, CA (US); Charles Stonewall Montgomery, Newport News, VA (US)

(73) Assignee: Revive Solutions, Inc., San Mateo, CA (US)

(*) Notice: Subject to any disclaimer, the term of this patent is extended or adjusted under 35 U.S.C. 154(b) by 0 days.

(21) Appl. No.: 15/834,835

(22) Filed: Dec. 7, 2017

(65) Prior Publication Data

US 2018/0161586 A1 Jun. 14, 2018

Related U.S. Application Data

(60) Provisional application No. 62/576,228, filed on Oct. 24, 2017, provisional application No. 62/566,896, (Continued)

(51) Int. Cl.
*A61N 1/00* (2006.01)
*A61N 1/39* (2006.01)
*A61N 1/04* (2006.01)

(52) U.S. Cl.
CPC ......... *A61N 1/3975* (2013.01); *A61N 1/3904* (2017.08); *A61N 1/3993* (2013.01);
(Continued)

(58) Field of Classification Search
CPC .. A61N 1/3904; A61N 1/3975; A61N 1/3981; A61N 1/3993; A61N 1/378; A61N 1/3782
See application file for complete search history.

(56) References Cited

U.S. PATENT DOCUMENTS 5,282,122 A 1/1994 Summer
5,285,779 A 2/1994 Cameron et al.
(Continued)

FOREIGN PATENT DOCUMENTS

AU 2017100994 8/2017
CN 101564574 10/2008
(Continued)

OTHER PUBLICATIONS

Beyer et al., U.S. Appl. No. 15/834,899, filed Dec. 7, 2017.
(Continued)

*Primary Examiner* — Scott Getzow
(74) *Attorney, Agent, or Firm* — Beyer Law Group LLP

(57) ABSTRACT

Several defibrillators, defibrillator architectures, defibrillator components and methods of operating defibrillators are described. In one aspect, a defibrillator (as for example an automated external defibrillator) that can be powered by a mobile communication device such as a smart cellular phone or a tablet computer is described. Utilizing a phone (or other mobile communication device) as the power supply for an external defibrillator allows the external defibrillator to be smaller and, in some circumstance, removes the need for a battery that stores sufficient energy for shock delivery—which would need to be checked and/or replaced on a regular basis. Additionally, when desired, certain control functionality, computation, data processing, and user instructions can be handled/presented by the mobile communications device thereby further simplifying the defibrillator design and improving the user experience. This architecture takes advantage of the nearly ubiquitous availability of smart phones, tablet computers and other mobile communication devices.

28 Claims, 19 Drawing Sheets

Related U.S. Application Data filed on Oct. 2, 2017, provisional application No. 62/433,067, filed on Dec. 12, 2016.

(52) U.S. Cl.
CPC ............ *A61N 1/046* (2013.01); *A61N 1/0492* (2013.01); *A61N 1/3943* (2013.01); *A61N 1/3968* (2013.01)

(56) References Cited

U.S. PATENT DOCUMENTS

| | | | |
|---|---|---|---|
| 5,330,526 | A | 7/1994 | Fincke et al. |
| 5,391,187 | A | 2/1995 | Freeman |
| 5,405,361 | A | 4/1995 | Persson |
| 5,544,661 | A | 8/1996 | Davis et al. |
| 5,579,234 | A | 11/1996 | Wiley et al. |
| 5,579,919 | A | 12/1996 | Gilman et al. |
| 5,591,213 | A | 1/1997 | Morgan |
| 5,596,427 | A | 1/1997 | Gliner et al. |
| 5,601,612 | A | 2/1997 | Gliner et al. |
| 5,607,454 | A | 3/1997 | Cameron et al. |
| 5,611,815 | A | 3/1997 | Cole et al. |
| 5,617,853 | A | 4/1997 | Morgan |
| 5,620,470 | A | 4/1997 | Gliner et al. |
| 5,645,571 | A | 7/1997 | Olson et al. |
| 5,658,316 | A | 8/1997 | Lamond et al. |
| 5,662,690 | A | 9/1997 | Cole et al. |
| 5,735,879 | A | 4/1998 | Gliner et al. |
| 5,749,904 | A | 5/1998 | Gliner et al. |
| 5,749,905 | A | 5/1998 | Gliner et al. |
| 5,779,166 | A | 7/1998 | Gliner et al. |
| 5,797,969 | A | 8/1998 | Olson et al. |
| 5,800,460 | A | 9/1998 | Powers et al. |
| 5,803,927 | A | 9/1998 | Cameron et al. |
| 5,818,703 | A * | 10/1998 | Jacobson ............ A61N 1/3925 363/21.13 |
| 5,836,978 | A | 11/1998 | Gliner et al. |
| 5,836,993 | A | 11/1998 | Cole |
| 5,879,374 | A | 3/1999 | Powers et al. |
| 6,005,370 | A | 12/1999 | Gustavson et al. |
| 6,016,059 | A | 1/2000 | Morgan |
| 6,047,212 | A | 4/2000 | Gliner et al. |
| 6,075,369 | A | 6/2000 | Morgan |
| 6,125,299 | A | 9/2000 | Groenke et al. |
| 6,208,896 | B1 | 3/2001 | Mulhauser |
| 6,327,497 | B1 | 12/2001 | Kirchgeorg et al. |
| 6,356,785 | B1 | 3/2002 | Snyder et al. |
| 6,405,081 | B1 | 6/2002 | Lyster et al. |
| 6,405,083 | B1 | 6/2002 | Rockwell et al. |
| 6,411,064 | B1 | 6/2002 | Brink |
| 6,417,649 | B1 | 7/2002 | Brink |
| 6,438,415 | B1 | 8/2002 | Powers |
| 6,438,417 | B1 | 8/2002 | Rockwell et al. |
| 6,441,513 | B1 | 8/2002 | Mulhauser |
| 6,441,582 | B1 | 8/2002 | Powers |
| 6,546,287 | B1 | 4/2003 | Havel et al. |
| 6,553,257 | B2 | 4/2003 | Snyder et al. |
| RE38,119 | E | 5/2003 | Mower |
| 6,778,365 | B2 | 8/2004 | Mulhauser |
| 6,839,590 | B2 | 1/2005 | Waltman |
| 6,873,133 | B1 | 3/2005 | Kavounas |
| RE38,897 | E | 11/2005 | Krenzel |
| 7,242,979 | B1 | 7/2007 | Kelly et al. |
| 7,570,994 | B2 | 8/2009 | Tamura et al. |
| 7,680,533 | B2 | 3/2010 | Garrett et al. |
| 7,904,152 | B2 | 3/2011 | Sullivan et al. |
| 7,920,917 | B2 | 4/2011 | Kelly et al. |
| 8,038,617 | B2 | 10/2011 | Maschke |
| 8,086,320 | B2 | 12/2011 | Saketkhou |
| 8,145,300 | B2 | 3/2012 | Powers |
| 8,179,087 | B2 | 5/2012 | Neumiller et al. |
| 8,489,187 | B2 | 7/2013 | Linder et al. |
| 8,565,871 | B2 | 10/2013 | Tuysserkani |
| 8,781,577 | B2 | 7/2014 | Freeman |
| 8,838,233 | B2 | 9/2014 | Kelly et al. |
| 8,965,501 | B2 | 2/2015 | Sullivan |
| 9,067,077 | B2 | 6/2015 | Drew et al. |
| 9,067,080 | B2 | 6/2015 | Einy |
| 9,138,592 | B2 | 9/2015 | Wu |
| 9,168,386 | B2 | 10/2015 | Schwibner et al. |
| 9,324,120 | B2 | 4/2016 | Braun |
| 9,415,230 | B2 | 8/2016 | Powers |
| 9,486,636 | B2 | 11/2016 | Schwibner et al. |
| 9,517,354 | B2 | 12/2016 | Schwibner et al. |
| 9,636,513 | B2 | 5/2017 | Kuo et al. |
| 9,889,311 | B2 * | 2/2018 | Horseman ............ A61N 1/3968 |
| 2003/0028219 | A1 | 2/2003 | Powers et al. |
| 2003/0078620 | A1 | 4/2003 | Waltman |
| 2004/0143297 | A1 | 7/2004 | Ramsey, III |
| 2004/0147972 | A1 | 7/2004 | Greatbatch et al. |
| 2005/0101999 | A1 | 5/2005 | Lyster et al. |
| 2007/0032830 | A1 | 2/2007 | Bowers |
| 2007/0270909 | A1 | 11/2007 | Saketkhou |
| 2008/0177341 | A1 | 7/2008 | Bowers |
| 2009/0100275 | A1 | 4/2009 | Chang et al. |
| 2009/0210022 | A1 | 8/2009 | Powers |
| 2009/0240297 | A1 | 9/2009 | Shavit et al. |
| 2010/0241181 | A1 | 9/2010 | Savage et al. |
| 2011/0130636 | A1 | 6/2011 | Daniel et al. |
| 2011/0245888 | A1 | 10/2011 | Badelt et al. |
| 2012/0087078 | A1 | 4/2012 | Medica et al. |
| 2012/0158073 | A1 | 6/2012 | Shao et al. |
| 2013/0109371 | A1 | 5/2013 | Brogan et al. |
| 2013/0167226 | A1 | 6/2013 | Lin |
| 2013/0238819 | A1 | 9/2013 | Oljaca et al. |
| 2013/0294118 | A1 | 11/2013 | So et al. |
| 2014/0107718 | A1 | 4/2014 | Foote et al. |
| 2014/0222095 | A1 | 8/2014 | Einy |
| 2014/0222096 | A1 | 8/2014 | Hu et al. |
| 2014/0317914 | A1 | 10/2014 | Shaker |
| 2015/0297906 | A1 | 10/2015 | Guichet |
| 2016/0210581 | A1 | 7/2016 | Braun |
| 2016/0250492 | A1 | 9/2016 | King et al. |
| 2017/0056682 | A1 | 3/2017 | Kumar et al. |
| 2017/0157415 | A1 | 6/2017 | Horseman et al. |

FOREIGN PATENT DOCUMENTS

| | | |
|---|---|---|
| CN | 101461983 | 6/2013 |
| CN | 103751910 | 4/2014 |
| CN | 105457165 | 4/2016 |
| CN | 105476068 | 4/2016 |
| DE | 4225892 | 2/1996 |
| EP | 1 530 983 | 5/2005 |
| JP | 2016-41239 | 3/2016 |
| KR | 10-1594750 | 2/2016 |
| WO | WO 2010/067373 | 6/2010 |

OTHER PUBLICATIONS

Montgomery et al., U.S. Appl. No. 15/834,911, filed Dec. 7, 2017.
Beyer et al., U.S. Appl. No. 15/835,152, filed Dec. 7, 2017.
Andrews et al., U.S. Appl. No. 15/835,222, filed Dec. 7, 2017.
Mercado et al., U.S. Appl. No. 29/626,141, filed Nov. 15, 2017.
Andrews et al., U.S. Appl. No. 29/626,256, filed Nov. 15, 2017.
Rapid Response Revival, "Australian Company World First with a Mobile Phone Defibrillator", www.rapidresponserevival.com/au/world-first-with-a-mobile-phone-defibrillator/, downloaded from the internet on Nov. 21, 2017.
Phillips, Heartstart Defibrillator, Owner's Manual, Edition 13, published Jan. 2014.
U.S. Office Action dated Apr. 27, 2018, from U.S. Appl. No. 15/834,899.
International Search Report and Written Opinion dated Apr. 23, 2018 from International Application No. PCT/US2017/065163.
Saliva, "Design Guide for a QR Flyback Converter", Infineon Technologies North America (IFNA) Corp., published in 2013.

* cited by examiner

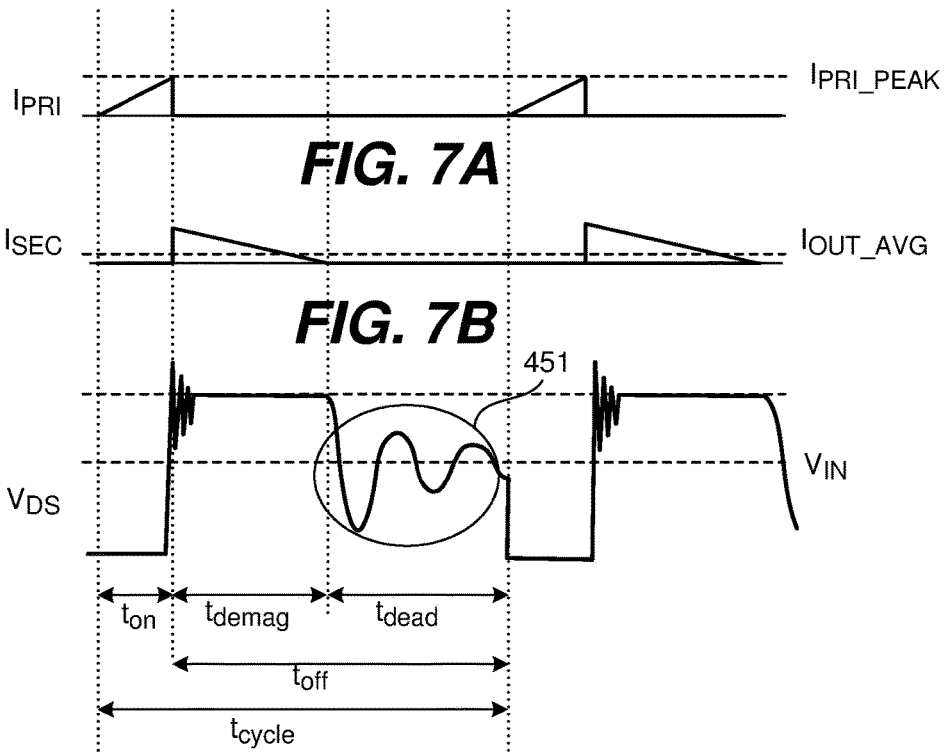
*FIG. 7A*
*FIG. 7B*
*FIG. 7C*
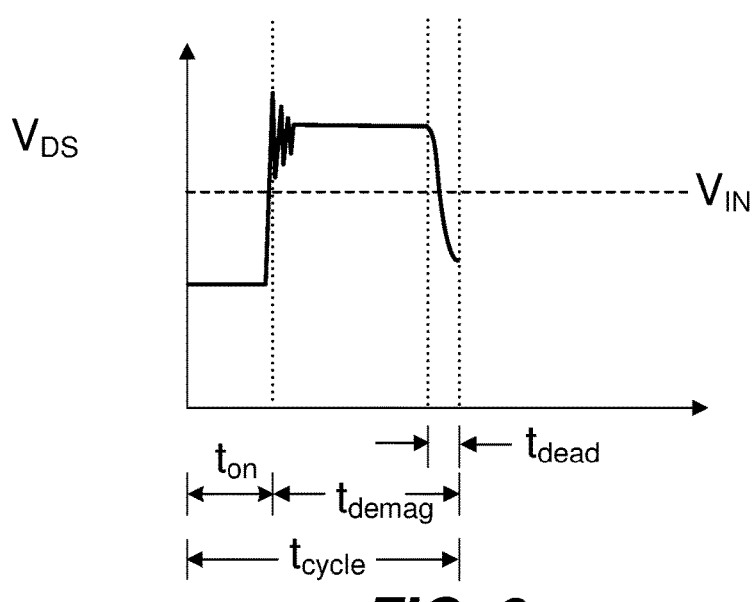
*FIG. 8*

DEFIBRILLATOR

CROSS-REFERENCE TO RELATED APPLICATIONS

The present application claims the priority of U.S. Provisional Patent Application Nos. 62/433,067, filed Dec. 12, 2016, 62/566,896 filed Oct. 2, 2017 and 62/576,228 filed Oct. 24, 2017, each of which is incorporated herein by reference in its entirety.

FIELD OF THE INVENTION

The present disclosure relates generally to defibrillators and many of the inventions described herein are particularly applicable to automated external defibrillators designed to be charged by and used in conjunction with a mobile communication device.

BACKGROUND

Sudden cardiac arrest is one of the leading causes of death. In the United States alone, roughly 300,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed such that they can be used by a lay person in situations where professional medical personnel are not available.

Given their potential to save lives, automated external defibrillators have been deployed in a relatively wide variety of public and private locations so that they are available in the event that a person in the vicinity goes in to cardiac arrest. By way of example, AEDs may be found in corporate and government offices, shopping centers, airports, airplanes, restaurants, casinos, hotels, sports stadiums, schools, fitness centers and a variety of other locations where people may congregate. Although the availability of AEDs has increased over the years, their relatively high cost tends to limit their placement and many locations including schools, sports fields, and a plethora of other places where people congregate don't have an on-site AED available. Furthermore, although many AEDs are considered "portable", most commercially available portable automated external defibrillators are bulky and heavy enough that they are rarely carried by people other than trained medical personnel. Thus there are many times, locations and events where no AED is available when a cardiac arrest incident occurs. Even when an AED is nearby when a sudden cardiac arrest incident occurs, the AED is often not used because either its presence is unknown or the device seems intimidating to bystanders who are reluctant to try to use a device that they are unfamiliar with.

Although existing AEDs work well, there are continuing efforts to develop AEDs that have characteristics likely to broaden the deployment and availability of automated external defibrillators.

SUMMARY

Several defibrillators, defibrillator architectures, defibrillator components and methods of operating defibrillators are described. In one aspect, a defibrillator (as for example an automated external defibrillator) that can be powered by a mobile communication device such as a smart cellular phone or a tablet computer is described. Utilizing a phone (or other mobile communication device) as the power supply for an external defibrillator allows the external defibrillator to be smaller and, in some circumstance, removes the need for a battery that stores sufficient energy for shock delivery—which would need to be checked and/or replaced on a regular basis. Additionally, when desired, certain control functionality, computation, data processing, and user instructions can be handled/presented by the mobile communications device thereby further simplifying the defibrillator design and improving the user experience. This architecture takes advantage of the nearly ubiquitous availability of smart phones, tablet computers and other mobile communication devices.

In some embodiments, the defibrillator is an AED suitable for use with an operator's personal smart phone and/or other types of personal communication or computing devices. In other embodiments, a dedicated smart phone is packaged together with the defibrillator. In still other embodiments, many of the features described herein are well suited for use in more conventional defibrillator architectures that are not necessarily intended for use in conjunction with a mobile communication device.

In various embodiments, the defibrillator includes a shock delivery capacitor and charging circuitry that includes voltage boosting circuitry that boosts the voltage of received current to charge the shock delivery capacitor.

In another aspect, various defibrillator charging circuitry is described. In some embodiments, the charging circuitry includes current regulating circuitry configured to maintain a current draw from a power source for the voltage boosting circuitry throughout the charging of the capacitor. In some embodiments, the current regulating circuitry includes a transitory electrical energy store that serves as a temporary store for electrical energy drawn for a power source during the voltage boosting circuitry's current shut-off intervals and as a supply of supplemental current to the voltage boosting circuitry during at least portions of the periodic current draw intervals. In some embodiments, the current regulating circuitry may include a digitally controlled current limiting Buck converter.

In another aspect, various flyback converter designs are described. In some embodiments, the voltage is boosted by a flyback converter—which in some specific embodiments takes the form of a valley switching flyback converter or more generally, a variable frequency flyback converter. In other embodiments, a maximum current through the primary coil of the flyback converter may be set programmably at the time of charging of the capacitor unit to help regulate the charging circuit's current draw. In some embodiments, the maximum primary coil current level is periodically adjusted during charging of the capacitor based at least in part on a then present measured voltage of the capacitor unit.

In another aspect defibrillators having various current regulating circuitry are described. In some embodiments, a defibrillator controller is arranged to set selected parameters of the current regulating circuitry in order to maintain a draw current from a mobile communication device (or other available power supply) at a level that is near, but does not exceed a maximum draw current associated with the mobile communication device. In some embodiments, such parameters may be set and reset by the defibrillator controller during charging of the capacitor unit to help maintain a desired current draw. Any of a number of different charging circuit parameters can be set by the defibrillator controller, as for example, the capacitance or inductance of the transitory electrical energy store, a maximum current level for the current draw from the power source (e.g., the mobile communication device) or for a particular component such as the primary coil of a transformer, a minimum current level for the current draw from the power source, etc.

In some embodiments, the current regulating circuitry includes a current sensor for sensing the current drawn from the power source and a controller (which may optionally be the defibrillation controller) that receives a sensed input current from the current sensor and turns an input switch of the voltage boosting circuitry on and off to maintain the current drawn from the power source within a designated range throughout the charging of the capacitor.

In a separate, more general aspect, some of the described circuit regulating circuits may be used to continuously draw current for voltage boosters used in devices other than defibrillators that are powered by a mobile communication device.

In another aspect a defibrillator may be arranged to automatically begin charging the capacitor when the defibrillator is initially activated. In some embodiments, the charging automatically begins when the defibrillator is initially connected to a mobile communication device. In other embodiments, the charging automatically begins when the defibrillator is manually activated by a user or in response to other specific triggers.

In various embodiments, the defibrillator may be connected to a mobile communication device through a connector cable that may be plugged into the mobile communication device. In other embodiments, the defibrillator and the mobile communication device are connected wirelessly—as for example through the use of inductive charging and the use of a short range wireless communication protocol.

In some embodiments the defibrillator does not include an energy storage device (such as a battery) that can be used to charge the discharge capacitor and is capable of holding sufficient energy to facilitate charging the capacitor to deliver a defibrillation shock to a patient. In other embodiments, the defibrillator includes an internal power supply arranged to provide power or additional power for charging the capacitor unit.

In some embodiments, an app is installed on the mobile communication device and may be used to at least partially control the defibrillator during its use.

In some embodiments the defibrillator includes a bleed circuit that slowly drains the capacitor such that the capacitor will not retain a charge for a prolonged period of time. In some embodiments, the bleed circuit is a voltage sensing circuit arranged to measure a voltage of the capacitor.

In yet another aspect, housings for defibrillators are described. In some embodiments, the defibrillator may include an elongated tubular housing having an external opening at a first end of the elongated tubular housing. Defibrillator electronics are positioned within the elongated tubular housing and a removable end cap may be provided to cover the external opening. In some embodiments, a pair of defibrillator pads and/or an electrical connector cable may be stored within the housing and be made accessible when the end cap is removed. In some embodiments, end caps are provided on both ends of the tubular housing.

In another aspect, in some embodiments, the elongated tubular housing has a substantially oval or stadium shaped cross section and/or has at least one flat edge.

In some embodiments, the end cap forms a watertight seal with the first end of the tubular housing. In some embodiments the end cap has a pull feature configured to be pulled to remove the end cap from the first end of the housing.

In some embodiments, the defibrillator electronics includes a first circuit board that carries low voltage components and a second circuit board that carries high voltage electrical components.

In some embodiments, the defibrillator further includes a battery pack that couples to the housing.

In yet another aspect, housings for defibrillators having integrated mobile devices are described. In one such embodiment, the housing has first second and third compartments. The first compartment holds a mobile communication device having a display screen that is exposed through a first external housing opening. The second compartment holds a pair of defibrillator pads which are accessible through a second external housing opening. The third compartment holds the defibrillator electronics. In some embodiments the housing has a gem shaped cross sectional area.

In another aspect, various methods of charging a defibrillator discharge capacitor are also described. In some embodiments, a maximum draw current for a discharge capacitor charging circuit is set based at least in part on a current delivery capability of a connected power supply, such as a connected mobile communication device. In some embodiments, the defibrillator is suitable for connection to multiple different types of devices having different current delivery capabilities. In such embodiments, different maximum draw currents can be specified for charging the capacitor unit to facilitate efficient use of such devices.

In some embodiments, a maximum current through a primary coil of a transformer is set at the time of charging based at least in part on a current delivery capability of the power supply. In some embodiments, the maximum current through the primary coil is changed during the charging of the defibrillator discharge capacitor based at least in part on a then present voltage or charge level of the defibrillator discharge capacitor.

In some embodiments, a variable electrical characteristic of a transitory electrical energy store is changed during charging of the capacitor unit based on the discharge capacitor charge level. In some embodiments, an input switch of the voltage boosting circuit is turned on and off to maintain the current drawn from the power source within a designated range.

In some embodiments, a continuous current draw from a power source is maintained for a voltage boosting circuit using a transitory electrical energy store. The transitory energy store serves has a temporary store for electrical energy drawn from the power source during the voltage boosting circuitry's periodic current shut-off intervals and as a supply of supplemental current to the voltage boosting circuitry during at least portions of the periodic current draw intervals.

In some embodiments, charging of a shock delivery capacitor is automatically initiated when the defibrillator unit is initially connected to the mobile communication device.

In yet another aspect, various approaches to controlling the delivery of a defibrillation shock are described. In some embodiment, a defibrillator controller determines the desired duration of a shock pulse based at least in part of a discharge capacitor voltage measurement taken during the delivery of the defibrillation shock pulse. In this approach, the impedance of the patient is effectively determined on the fly during shock delivery using the voltage measurements and known characteristics of the discharge capacitor.

In yet other aspects, various apps and/or other software or firmware based control routines are described that are well suited for controlling various aspects of the use and/or operation of a defibrillator. An app or other suitable software construct can have programmed instructions stored in the memory of a computing device such as a mobile communication device.

In some embodiments, an app on a mobile communication device is configured to transmit an indication of a parameter to the defibrillator that is indicative of, or can be used by the defibrillator to determine, the mobile communication device's current delivery capabilities. In some embodiments, the app includes programmed instructions for analyzing heart rhythms received from the defibrillator unit to determine whether a patient has a shockable heart rhythm.

In some embodiments, the app is configured to automatically authorize delivery of current from the computing device to the defibrillator unit in response to the connection of a defibrillator unit to the computing device.

In some embodiments, a defibrillator control app is configured to generate an event history log that records a history associated with the use of an associated defibrillator for a particular event. The event history log may include a shock history that includes an indication of the number of shocks delivered, an indication of the energy charge utilized in each applied shock associated with the event and the time that each applied shock associated with the event was administered. The app can also be configured to display an event history GUI element on a display screen of the mobile communication device. Selection of the event history GUI element causes an event history frame to be displayed on the display screen. The event history frame shows the number of shocks delivered, the energy charge utilized in each applied shock associated with the event and the time that each applied shock associated with the event was administered.

BRIEF DESCRIPTION OF THE DRAWINGS

The invention and the advantages thereof, may best be understood by reference to the following description taken in conjunction with the accompanying drawings in which:

FIGS. 7A-7C are graphs respectively illustrating the primarily coil current, the secondary coil current and the switch drain voltage associated with a charging cycle of the representative flyback converter illustrated in FIG. 6.

FIG. 8 is a graph illustrating the switch drain voltage associated with a charging cycle of a valley switching flyback converter.

In the drawings, like reference numerals are sometimes used to designate like structural elements. It should also be appreciated that the depictions in the figures are diagrammatic and not to scale.

DETAILED DESCRIPTION

Figure 1:
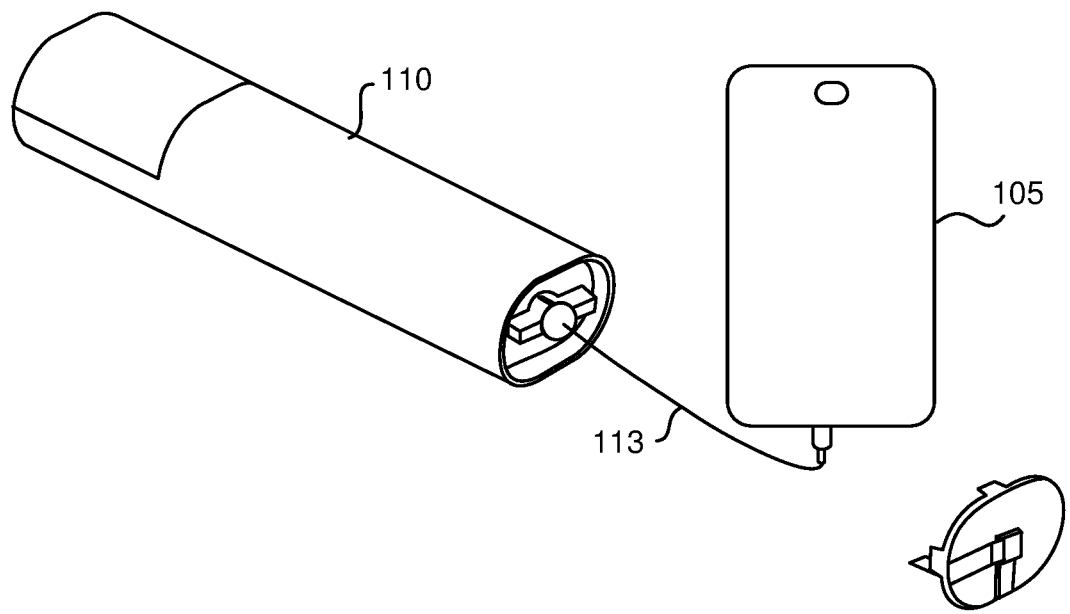
FIG. 1 is a diagrammatic illustration of an automated external defibrillator ready for deployment in accordance with one embodiment of the invention.

Referring initially to FIG. 1, a portable defibrillator architecture in accordance with one embodiment of the invention will be described. The illustrated architecture is well suited for use in automated external defibrillators (including both semi-automatic and fully automatic defibrillators) although it may also be used in manual defibrillators and hybrid defibrillators that may be used in either automated or manual modes. The core of the portable defibrillator system 100 is a defibrillation unit 110 which is preferably used in conjunction with a mobile communication device 105 such as a cell phone, a tablet computer, a personal digital assistant (PDA) or other portable computing device. The system 100 also includes a connector cable 113 and pair of defibrillator pads 116. In the illustrated embodiment, the mobile communication device takes the form of a smart phone such as a Samsung Galaxy or an Apple iPhone. However, in other embodiments, a wide variety of other mobile communication devices may be used in place of the smart phone. Power for the defibrillation unit 110 is obtained from the phone 105, which eliminates the need to provide batteries or other long term energy storage devices that store sufficient energy for shock delivery as part of the defibrillation unit.

In some preferred embodiments, the defibrillation unit 110 is designed to be used in conjunction with an app 108 that is installed, or installable on the mobile communication device. This permits use of the processing power of the phone to handle some of the signal processing, control and user interface functions required of the defibrillator system.

The defibrillator unit 110 houses electrocardiography circuitry for detecting electrical activity of a heart of a patient and shock delivery circuitry for delivering a defibrillation shock to the patient when appropriate. The defibrillation unit 110 preferably also houses the connector cable 113 and the defibrillator pads 116 when the unit is stored. To use the defibrillator, the connector cable 113 is plugged in to the I/O connector on the phone 105. The defibrillation unit 110 is preferably configured to begin charging the shock delivery circuitry as soon as it is plugged into the phone. In the illustrated embodiment, connector cable 113 takes the form of a micro USB cable because the illustrated phone 105 has a micro USB connector. However in other embodiments, the cable can include any form that is appropriate for connection to the phone's I/O connector—as for an example, a lightening cable/connector, any other type of USB connector, including a USB-C cable/connector, a 30 pin dock cable/connector, etc.

Any of a variety of commercially available defibrillator pads may be used as defibrillator pads 116. Typically the defibrillator pads are adhesive so that they can be securely attached to a patient at the time of a sudden cardiac event. If desired separate pads can be provided for adult and pediatric applications.

The medical community has established a variety of recommended external defibrillation shock protocols. These protocols typically call for the delivery of an electrical shock on the order of 120-200 joules at a voltage on the order of 1400-2000V for an adult when a biphasic defibrillator is used. More energy, as for example 200-360 joules is typically required if a monophasic defibrillator is used. Considerably lower shock intensities are recommended for pediatrics applications. The recommended shock guidelines can vary with the age/size of the patient and the nature of the heart rhythms that are detected. The defibrillator electronics can be configured to deliver any shock protocol deemed appropriate for the specific event.

Electronics

Figure 2:
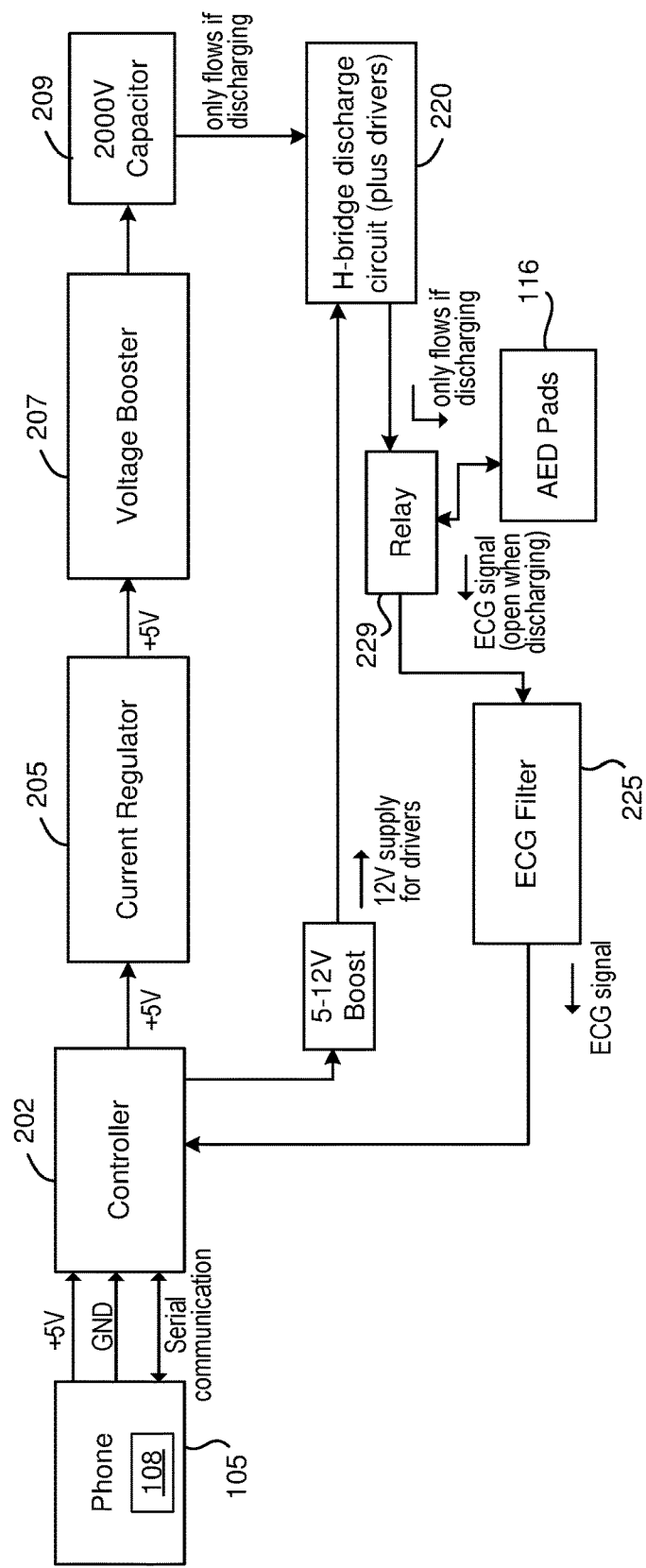
FIG. 2 is a circuit block diagram illustrating an electronics architecture suitable for use in a defibrillator such as the AED of FIG. 1.

FIG. 2 is a block diagram illustrating a first electronics architecture and associated components suitable for use in a defibrillator. In the illustrated embodiment, the electronic components include a controller 202, a current regulator circuit 205, a voltage booster 207 (which may have multiple stages), a high voltage capacitor 209 for temporarily storing sufficient electrical energy suitable to provide a defibrillation shock, discharge control circuitry 220, ECG sensing/filtering circuitry 225 and relays 229. The current regulator 205 and voltage booster 207 which cooperate to control the charging of the capacitor 209 are sometimes referred to herein as a charging circuit 208.

When the defibrillator unit 110 is connected to the phone via connector cable 113 there are at least three lines over which connections are made. They include a power supply (typically, 5V), a ground (GND) and one or more serial communication lines between the defibrillator controller 202 and a processor on the phone. The controller 202 (which may take the form of a microprocessor) communicates with the processor on the phone via the serial line(s) on the connector cable.

In one particular implementation, a USB OTG (on the go) connection is made, which allows the phone to essentially become the "host" that is able to control the processor on the defibrillator. The internal wiring of various USB OTG cables may vary. For example, a type B micro-USB OTG cable is a five pin USB plug. It has +5V, GND, two lines for Data+ and Data− that work together to become the serial communication. The fifth line is the "sense" line that indicates that the device is in host mode. In another example, a type C USB OTG cable has 12 pins, again with pins for GND, power and serial communication.

The controller 202 is configured to control the state of relay 229 and to switch the various components of the defibrillator between the ECG reading and discharge states. The controller 202 also cooperates with the app 108 to manage and control the AED during use. In applications where the app 108 provides primary control over the process flow, the microprocessor acts as the "middle man" that orchestrates the electronic components in accordance with the app's instructions. In such an embodiment, the microprocessor 202 receives commands from the phone, and returns to the phone whatever has been asked of it. For instance, if the phone asks for the capacitor charge, the processor 202 will return an indication of the scaled voltage. If the phone asks for confirmation that the electrode pads are connected, the microprocessor will return an indication verifying their connection. If the phone asks for the ECG reading, the microprocessor will send the ECG signal being taken from the pads attached to the body back over the serial line. If the phone instructs a shock to be delivered, the microprocessor will set the appropriate pins in order to drive the HV system to deliver the shock. In other embodiments, the controller 202 may orchestrate more of the overall process flow.

The power supply (typically, but not necessarily 5V) is used both to power the electronics carried on the defibrillator unit 110 and to charge the high voltage capacitor 209. Thus, voltage booster 207 is arranged to boost the voltage from 5V to the desired operational voltage of the discharge capacitor 209, which in the described embodiment may be on the order of approximately 1400V-2000V (although the defibrillator may be designed to attain any desired voltage). In a particular embodiment a multi stage boost converter is used with a first stage being used during lower voltage periods of the charging and the second stage being used during higher voltage periods of the charging. By way of example, in one implementation each stage is a proportional boost converter circuit and the stages are arranged in parallel. The first stage is used to charge capacitor 209 to an intermediate threshold voltage such as 800 volts, and the second stage is used to charge the capacitor at voltages above the threshold. An advantage of using multiple stages is that each stage can boost more efficiently in its operational range. Of course, the specific threshold(s) used and the number of stages employed may vary widely.

Figure 4:
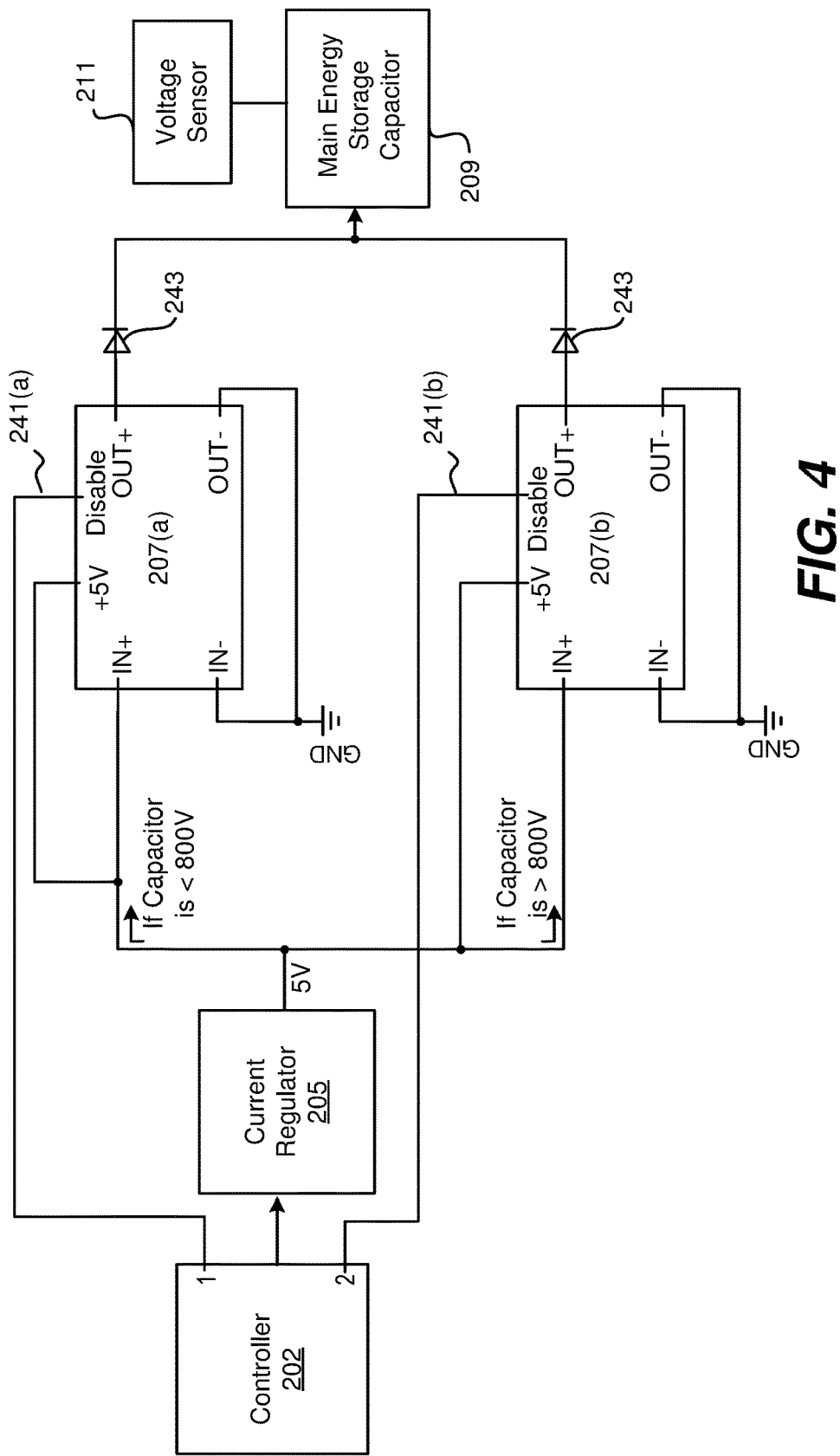
FIG. 4 is a schematic circuit diagram of a parallel boost converter suitable for use in the described defibrillators.

By way of example, FIG. 4 is a schematic circuit diagram of a suitable two stage parallel boost converter. In the illustrated embodiment, parallel boost converters 207(*a*) and 207(*b*) are each fed 5V power from current regulator 205. Each boost converter 207(*a*) 207(*b*) has a corresponding enable line 241(*a*), 241(*b*) coupled to the controller 202. The controller directs when each of the boost converters are turned on using their respective enable lines 241. When the boost converter is turned on, its voltage boosted output is fed to the capacitor 209 to thereby charge the capacitor. In the illustrated embodiment, diodes 243 are provided to prevent current from flowing in the reverse direction, although it should be appreciated that other suitable structures or arrangements may be used to accomplish the same function. The boost converters 207 may be implemented using discrete circuitry, integrated circuit boost converter chips or in other suitable manners. By way of example, in some implementations a FS20 module available from XP Power may be used.

In other embodiments the voltage boosting can be accomplished in a single stage or in multiple stages and the magnitude of the voltage boost provided by each stage may be varied as appropriate. In still other embodiments, the stages can be operated in parallel. The two stage boosting described has some cost/efficiency advantages based on commercially available parts.

The current regulator 205 ensures that the charging circuit does not draw more current than the mobile communication device can provide. This is important because many cellular phones and tablet computers have safety circuits that cut off the delivery of electrical current if too much current is drawn at any time. If the defibrillator unit 110 trips the safety circuit by drawing more current than permitted by the attached phone, the phone's safety circuit will cut off power from being drawn from the I/O port and it may be some time before connector power is restored—which is undesirable. At the same time, during charging of the capacitors, it is desirable to draw very close to as much power as the phone has the ability to provide because the charge time is inversely proportional to the drawn current. Therefore, restricting the charging current draw to a level noticeably below the maximum current that can be drawn from the phone will cause unnecessarily slow charging. Thus, a goal for the current regulator 205 is to maintain the current drawn from the phone at a level that is very close to, but is assured not to exceed, the maximum current that is known to be obtainable from the phone. Preferably, current is drawn substantially continuously from the phone, rather than in periodic bursts dictated by the voltage boosting circuitry as is common in most transformers and other voltage boosting circuits.

By way of example, limiting the charging current to just under 500 mA has been found to work well with most older smart phones including phones ranging from various older Blackberries to Samsung Galaxy S5/S6. This is because many such phones utilize USB 2.0 or similar connectors and the USB 2.0 specification calls for the delivery of 500 mA at 5V. Even these current draw rates facilitate charging the capacitor 209 sufficiently to deliver a 150 joule defibrillation shock within an appropriate period based on the expected set-up time for defibrillation for the first shock and the recommended interval between shocks for any subsequent shocks that may be advised (defibrillation shocks are typically recommended every two minutes if necessary during resuscitation). Most newer phones support significantly higher current draw rates which facilitate even faster charging. By way of example, phones utilizing USB 3.0 connectors are typically able to continuously deliver 900 mA at 5V and many modern phones support significantly higher current draws.

In the illustrated embodiment, a digitally controlled current regulator 205 is positioned between the controller 202 and the boost converter 207 so that it controls the current being delivered to the boost converter, although in other embodiments it may be placed at any other suitable location.

The current regulator 205 may take a variety of forms as long as it accomplishes the intended functions of (1) maintaining the input current at a generally stable level that is close to, but never exceeds the maximum current that can be delivered by the phone, and (2) keeps parasitic power losses low. A digitally controlled current limiting Buck converter that is well suited for use as current regulator 205 is illustrated in FIG. 3.

Figure 3:
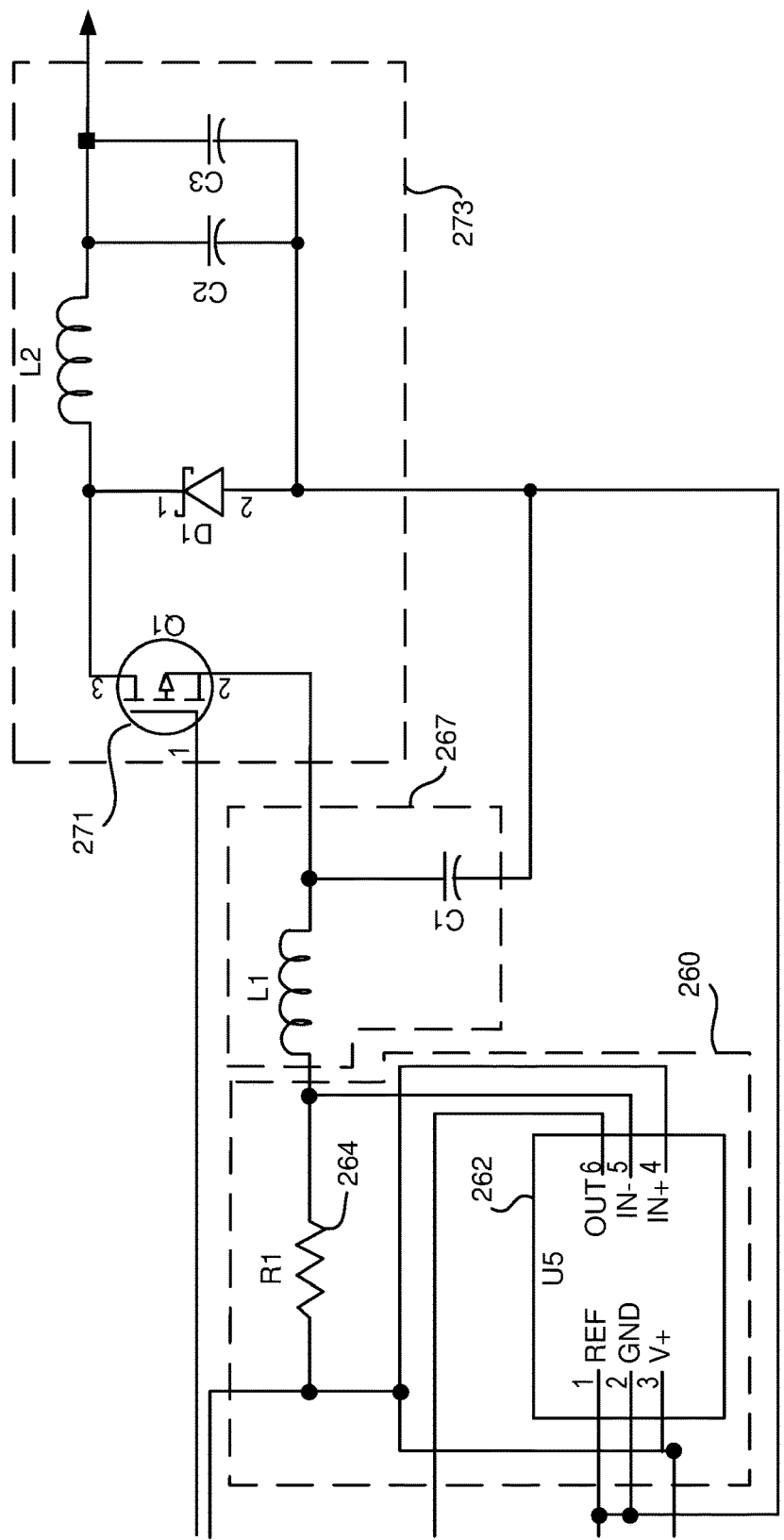
FIG. 3 is a schematic circuit diagram of a digitally controlled current limiting Buck Converter.

In the embodiment illustrated in FIG. 3, the current regulator 205 is a digitally controlled current limiting Buck converter that includes a current sensor 260 (R1, U5) that detects the input current level, an LC circuit 267 (L1, C1) and a Buck converter 273 (271,D1,L2,C2,C3). In some embodiments, the current sensor 260 may be implemented using a current sensing chip 262 (U5) that detects the voltage drop across a small resistor 264 (R1). The resistor 264 is preferably very small—just enough for the current sensing chip to be able to detect the voltage drop across the resistor in order to determine the current flow while providing minimal power loss (as for example less than $0.1\Omega$). The sensed current is communicated to a suitable controller, which in the described embodiment is incorporated into defibrillator microcontroller 202. With this approach, the controller always knows the instantaneous level of current being drawn by the voltage booster 207.

The LC circuit 267 (L1, C1) serves as an input for an input switch 271 for Buck converter 273 (O1,D1,L2,C2,C3). Buck converters are generally known to be efficient step down voltage converters. The voltage is stepped down while stepping up current with only a small loss of power. In the illustrated embodiment, input switch 271 takes the form of a MOSFET, although other switches may be used in other embodiments. The on/off state of MOSFET switch 271 is controlled by a current regulator controller—which in this case is incorporated into the functionality of microcontroller 202.

In order to charge the defibrillator capacitor 209, the MOSFET switch 271 is turned on and current begins flowing from the source (e.g. the connected phone) through resistor 264 and inductor L1 into the Buck converter 273. The presence of inductor L1 causes the current to rise in a generally exponential manner. The current sensing chip 262 detects the current being drawn by the voltage boost converter 207 and continually reports the value to controller 202. When the current approaches the maximum permissible current threshold, switch 271 is turned off by controller 202. At this stage current continues to flow through the inductor L1, passing now into LC circuit capacitor C1 which begins to charge. As LC circuit capacitor charges, its back voltage increases, thereby causing the current to flow more slowly. When the current drops to a slightly lower threshold, the switch 271 is turned back on by controller 202, at which point current flows into the Buck converter 273 from both the inductor L1 and the LC circuit capacitor C1. With the Buck converter switch 271 open, current through the inductor L1 begins to rise again in an exponential manner until it again approaches the maximum permissible current threshold at which point the switch 271 is turned off again. This process is repeated throughout the defibrillator charging process.

The switch 271 can be switched very quickly. By way of example, in some implementations a clock rate on the order of a megahertz is used (although it should be appreciated that the actual clock rate can vary widely). Therefore the upper and lower current thresholds can be quite close to each other in magnitude so that the charging current remains relatively stable near the maximum permissible draw current for the connected mobile device 105. For example, if the maximum permissible draw current is 500 mA, then the upper threshold can be set at on the order of 495 mA and the lower threshold can be set at on the order of 485 mA, which results in a current draw that oscillates between 485 and 495 mA. Of course, the specific upper and lower thresholds used may be varied based on any design criteria considered important to the designer.

Several features of this arrangement are particularly noteworthy. Initially, current is continuously drawn from the power supply (e.g. the mobile device battery) during the discharge capacitor charging process. This contrasts with traditional defibrillator designs in which the power to charge a discharge capacitor is drawn from the power supply in periodic intervals. Additionally, the current is drawn from the power supply at a relatively constant rate, which again is quite different than conventional designs.

Since the controller 202 directs the operation of switch 271, it can readily adjust the thresholds used without requiring any changes to the current regulating circuitry. Thus, for example, if the connected mobile device 105 is capable of delivering 900 mA of current, the thresholds used by the controller can be set appropriately to maintain a relatively constant current draw near 900 mA—as for example, an upper threshold of 895 mA and a lower threshold of 885 mA. In practice, any appropriate current limit can be enforced using the described approach. The ability to programmably set a maximum or desired draw current from the power supply used to charge the discharge capacitor at the time of use is also quite different than conventional designs. It should be apparent that in appropriate circumstances, the maximum or desired draw current can be set to a value that is close to the maximum continuous draw current authorized by the device (e.g., the mobile device) powering the charging of the discharge capacitor.

In the specific example given above, the current regulator 205 is instructed to maintain a constant current near 500 mA which corresponds to the maximum current draw specified by the USB-2.0 connector specification and thus it is believed that most smart phones are capable of supplying at least 500 mA of current at 5 volts. However, other popular connector specifications have higher current limits and most modern phones/mobile devices permit higher current draws (often significantly higher current draws). For example, USB-3.0, which is used in many newer phones, supports a current draw of up to 900 mA at 5V which significantly reduces charging time. USB-C connector cables support even higher current draws—as for example draw currents of 1.5 or 3.0 Amps at 5V.

It should be appreciated that the described current regulator 205 can be used to efficiently control the power draw from a mobile communication device in a variety of other applications as well (e.g., in devices other than defibrillators which seek to draw power from a smart phone or other mobile communication device)—and/or in other applications where a device that needs power may be couple to power supplying devices capable of delivering different current levels.

Some mobile communication device providers such as Apple require permission for an external device to draw power from their phones and tablet computers and are understood to have the ability to set higher current draws. Therefore, some manufactures may be willing to set higher current draws for approved medical applications such as the described defibrillators. An advantage of the digitally controlled current limiter described above is that the drawn current can be set to any desired/appropriate level. Thus, for example, if the defibrillator unit 110 is connected to a device capable of delivering 900 mA, then the app 108 can instruct defibrillator controller 202 to set the current limiter to a charge current of nearly 900 mA current—which would shorten the charging time to a designated charge level a corresponding amount. In general, the current limit can be set to any level that is appropriate for the connected device. In some embodiments, the app 108 and/or the defibrillator controller includes a lookup table or other suitable construct that can be used to find the appropriate current draw level for any particular type of mobile communication device that is connected to the AED.

A voltage sensor 211 is provided to read the voltage of the capacitor 209. The voltage sensor may take the form of a voltage divider or any other suitable form. This capacitor voltage reading is utilized to determine when to switch between boost stages and when the AED is charged suitably for use. The sensed voltage is provided to controller 202 which is configured to transmit a ready for discharge message to the phone 105 over cable 113 when the capacitor 209 is charged sufficiently to deliver a defibrillation shock. In other embodiments, the controller 202 can transmit the sensed capacitor voltage to the phone 105 which may have logic for determining when the required discharge voltage is attained. It should be appreciated that the capacitor 209 can be charged to any desired level. This is important because different defibrillation protocols advise different voltage and/or energy level shocks for different conditions. Furthermore, if the initial shock is not sufficient to restart a normal cardiac rhythm, recommended treatment protocols often call for the use of progressively stronger impulses in subsequently administered shocks (up to a point).

Figure 5A:
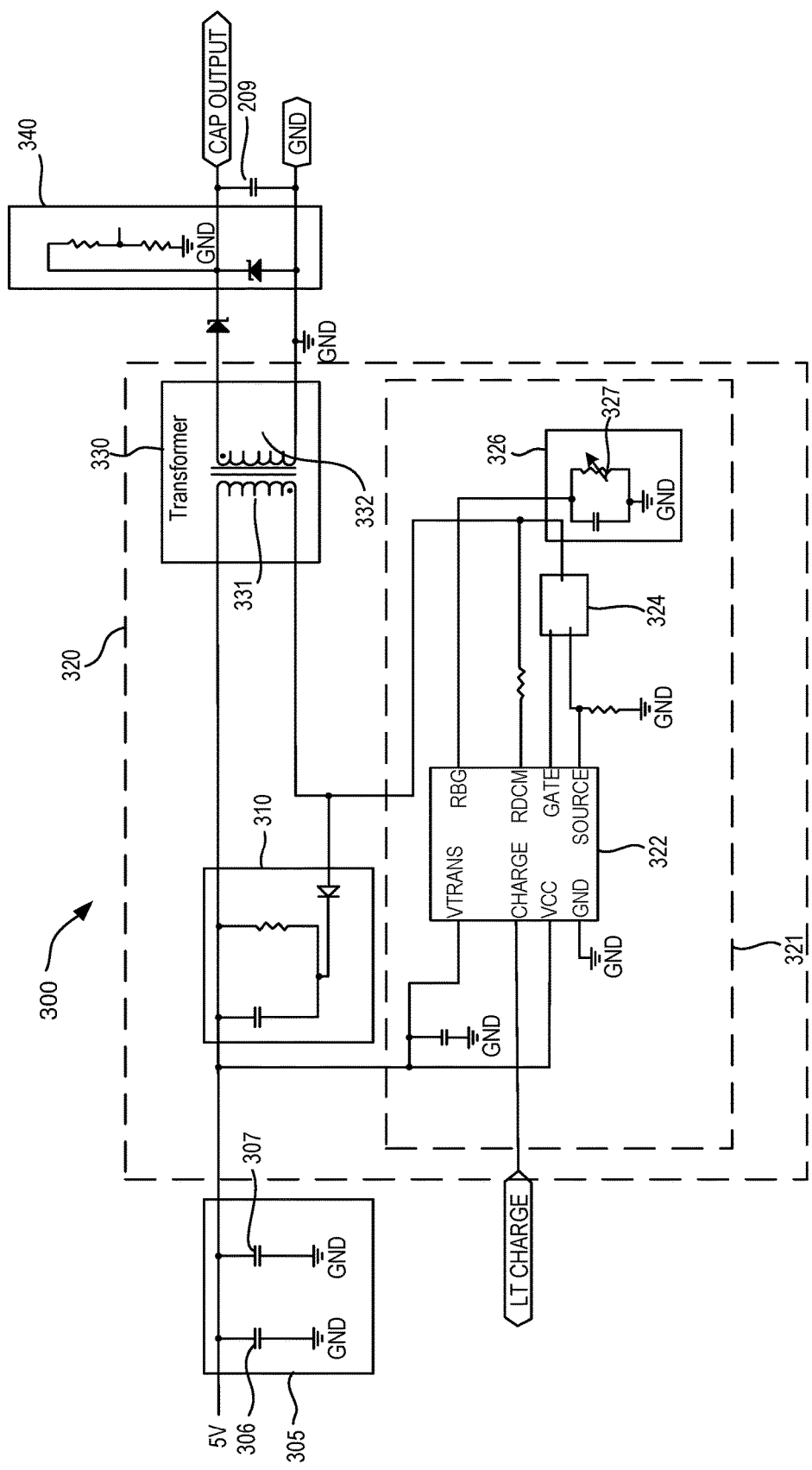
FIG. 5A is a schematic circuit diagram of a valley switching flyback converter based discharge capacitor charging system in accordance with another embodiment.

Referring next to FIG. 5A, an alternative discharge capacitor charging circuit will be described. In this embodiment, a flyback converter is used as the voltage booster circuitry 207 in place of the boost converters to charge discharge capacitor 209. In some preferred embodiments, a valley switching flyback converter is used.

In the embodiment illustrated in FIG. 5A, capacitor charging circuitry 300 includes a transitory electrical energy store 305, a flyback converter 320, and capacitor voltage sensor 340.

The transitory electrical energy store 305 serves as a temporary store for electrical energy drawn from the mobile device so that current can continue to be drawn from the mobile device even when current to the transformer is transitorily turned off as part of the flyback converter control. Stored energy is drawn from the transitory electrical energy store to supplement the draw current during periods in which the transformer is turned on such that the total current fed to the transformer while the primary transformer coil is on is actually higher than the current drawn from the mobile device itself. In some embodiments (as for example, the embodiment of FIG. 5A), the transitory electrical energy store 305 takes the form of a stacked set of capacitors, although it should be appreciated that in other embodiments, different circuitry can be used to accomplish similar functionality. For example, in some embodiments, one or more inductors can be arranged in conjunction with one or more capacitors to form the transitory electrical energy store—as is illustrated, for example, in the transitory electrical energy store (the LC circuit 267) utilized in the digitally controlled current limiting Buck converter of FIG. 3. In still other embodiments one or more inductors may be used to form the transitory electrical energy store.

The flyback converter 320 boosts the voltage from the voltage output from the mobile device (typically approximately 5V) to a high voltage suitable for charging the shock discharge capacitor 209 to its operational voltage. As previously discussed, the discharge capacitor 209 is typically charged to a voltage on the order of approximately 1400V-

2000V (although the discharge capacitor may be designed to attain any desired voltage). In some embodiments valley detection flyback converter control is used.

In a particular embodiment illustrated in FIG. 5A, the flyback converter 320 includes a transformer controller 321 and transformer 330. The transformer controller 321 includes a valley detection switching controller 322, a switch 324, and a maximum transformer current control circuit 326. In some embodiments, the valley detection switching controller 322 takes the form of a dedicated integrated circuit chip such as the LT3750 capacitor charging controller available from Linear Technologies (Analog Devices). The switch 324 is arranged to turn the transformer 330 on and off. When the switch 324 is turned on, current is drawn into the primary coil 331 of transformer 330. When the switch is turned off, current no longer flows into the primary coil. The switch 324 typically takes the form of a FET such as a MOSFET, although other structures can be used as the switch in other embodiments. Although specific circuitry and chip are illustrated, it should be appreciated that other flyback converter control circuits or control chips, can be used in other embodiments.

In the illustrated embodiment, the flyback converter 320 also includes a snubber circuit 310 that is arranged to smooth voltage transitions during switching of the transformer 330, although it should be appreciated that in other embodiments, different circuitry can be used to accomplish the desired functionality.

Figure 6:
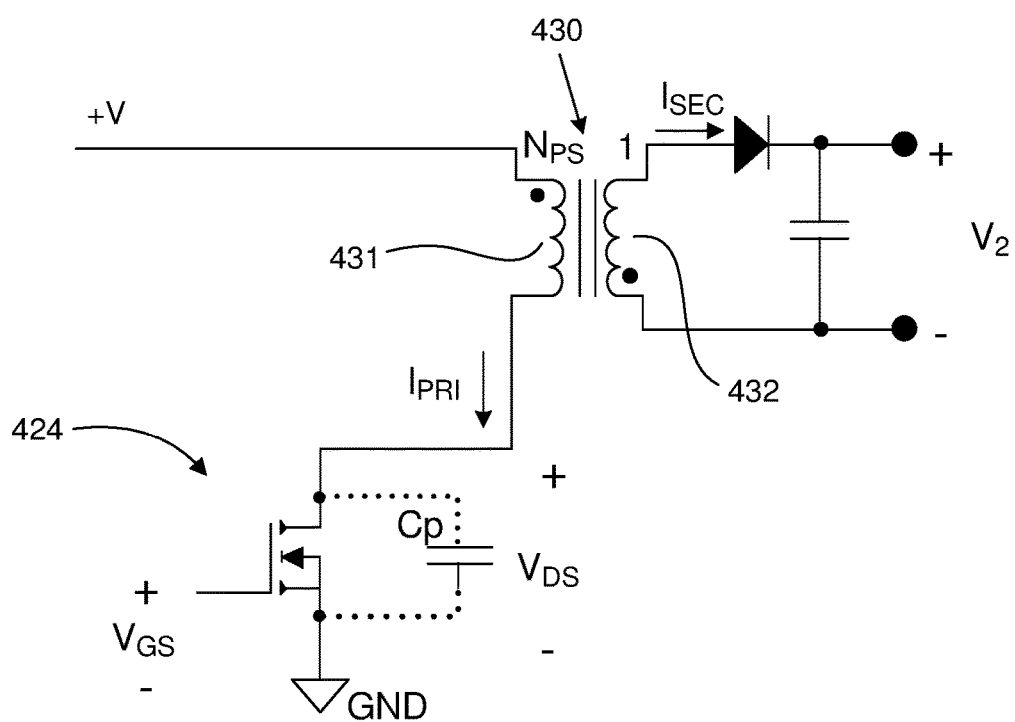
FIG. 6 is a circuit diagram illustrating a representative flyback converter.

Referring next to FIGS. 6-8, the advantages of valley detection control will be described. FIG. 6 illustrates a traditional flyback converter circuit in which a MOSFET switch 424 is used to control the flow of current through transformer 430. The input side of primary coil 431 is connected to power (e.g. 5V) and the output side of primary coil 431 is connected to ground through switch 424. When switch 424 is turned on, current flows through the primary coil 431. When the switch 424 is first turned on, current $I_{pri}$ begins flowing through the primary coil and increases until the peak primary coil current $I_{pri\_peak}$ is achieved as seen in FIG. 7A. At that stage, the switch 424 is turned off and current $I_{sec}$ begins flowing out the secondary coil 432 and gradually decays as seen in FIG. 7B. Once the transformer is effectively discharged, the secondary coil current $I_{sec}$ stops flowing and voltage on the drain side of MOSFET switch 424 will experience a resonant ringdown 451 as illustrated in FIG. 7C. Traditionally, the switch 424 is kept off for a designated waiting (ringdown) period ($t_{dead}$) that is considered long enough to ensure that that the MOSFET drain voltage $V_{ds}$ will always have settled to effectively be equal to the input voltage, or at least be below a designated voltage. This is important because if the drain voltage $V_{ds}$ is higher than the bus voltage (in the context of defibrillator unit 110, the input voltage of the phone) when the switch 424 is turned back on, high switching losses will result, whereas if the drain voltage $V_{ds}$ is lower than the bus voltage, low switching losses and high efficiency will result.

After the waiting period is over, the switch 424 may be turned back on and the process is repeated. The period between the time when current $I_{sec}$ stops flowing through the secondary coil 432 and when the switch 424 is turned back on is effectively dead time ($t_{dead}$) in which the transformer is not performing useful work. In practice, the dead time in many flyback converter designs is often a ($t_{dead}$) significant percentage (e.g., greater than 40%) of the total flyback converter cycle period ($t_{cycle}$) which includes (a) the time ($t_{on}$) in which switch 424 is on with current flowing through the primary coil; (b) The period ($t_{demag}$) which current $I_{sec}$ flows (out the secondary coil 432; and (c) the waiting period ($t_{dead}$).

Valley detection is used to reduce the waiting period ($t_{dead}$) before the switch 424 is turned back on—which has the effect of improving the overall charging efficiency. With valley detection, the trough(s) that occur in the ringdown 451 are detected. The switch 424 is turned on once a trough (valley) (preferably one of the first troughs) is detected thereby beginning the next flyback converter cycle after a much shorter waiting period ($t_{dead}$). This can significantly improve the charging efficiency of the overall capacitor charging circuit, both by limiting $t_{dead}$ as well as facilitating low switching losses when the next cycle is initiated. Therefore, the charging cycle may look more like the cycle illustrated in FIG. 8. FIG. 8 illustrates an example in which the first valley is detected which may occur in some circumstances. In other circumstances, the valley detector may actually detect and switch on a subsequent valley (e.g., the second or third valley) which still significantly reduces the ringdown waiting period.

As will be appreciated by those familiar with advanced flyback converter design, a flyback converter operates in a discontinuous conduction mode (DCM). Valley switching is a specialized form of DCM and is sometimes also referred to as a variable frequency flyback converter. A quasi-resonant flyback converter is a specific form of valley switching operation, where the switch 424 is always turned on when the first valley is detected, thereby achieving the lowest possible switching losses. Although only valley detection based discontinuous mode flyback conversion has been described in detail, it should be appreciated that other types of converters, including other discontinuous mode flyback converters or continuous conduction mode (CCM) flyback converters may be used in other embodiments.

Returning to FIG. 5A, the illustrated embodiment, the capacitor charging controller 322 is designed so that the maximum primary coil current $I_{pri\_peak}$ can be programmably set by defibrillator controller 202. In the illustrated embodiment, this is accomplished by maximum transformer current control circuit 326 which is an RC circuit having a variable resistor 327. The resistance of the variable resistor 327 is set by defibrillator controller 202, which thereby sets the value of maximum current control pin RBG on capacitor controller 322.

In practice, the transitory electrical energy store 305 cooperates with aspects of the flyback converter control to provide the desired current regulating functionality (e.g., to keep drawing current suitable for use in charging the discharge capacitor—preferably at a level relatively close to a designated current draw—even while the primary coil of the flyback converter is turned off, to prevent the current drawn from the mobile device from exceeding a specified limit).

With the illustrated circuitry, the draw current from the mobile device will be affected by several factors including the maximum primary coil current $I_{pri\_peak}$, the present voltage of the capacitor 209, and the structure of the transitory electrical energy store 305. For any given capacitor charge level (and with all other factors being fixed), setting the maximum primary coil current $I_{pri\_peak}$ in the illustrated circuitry will cause a predictable current ($I_{draw}$) to be drawn from the mobile device. Therefore, for any given state, setting the maximum primary coil current $I_{pri\_peak}$ has the effect of setting the maximum draw current ($I_{draw}$) and programmably controlling the maximum primary coil current $I_{pri\_peak}$ has the effect of programmably controlling maximum draw current ($I_{draw}$).

In general, for a given maximum primary coil current $I_{pri\_peak}$, the average current drawn by the flyback converter will decrease as the voltage level of discharge capacitor 209 increases during charging. Therefore, if the maximum primary coil current $I_{pri\_peak}$ is maintained at a fixed level, the draw current will decrease somewhat in a predictable manner as the capacitor charges. In some embodiments, the defibrillator controller 202 is arranged to occasionally adjust the maximum primary coil current $I_{pri\_peak}$ as the capacitor charges in a manner that maintains the draw current at close to the designated maximum allowable draw current. In a simple implementation, a lookup table or other suitable data structure may be used to identify the appropriate values for the variable resistor 327 at different charge levels and the defibrillator controller can occasionally direct adjustment of the variable resistor in a manner that maintains close to the desired draw current. Of course, in other implementations, the specific parameter settings that are adjusted and/or the data structures or algorithms used to determine the desired settings may be varied as appropriate for such embodiments. By adjusting the charging parameters as the discharge capacitor 209 charges, the discharge capacitor can be charged more rapidly without exceeding the maximum allowable draw current.

In the illustrated embodiment, the transitory electrical energy store 305 includes two capacitors 306, 307 which have significantly different capacitances, although it should be appreciated that three or more stacked capacitors may be used in other embodiments. Typically the capacitors will have significantly different capacitances and are sized based on the needs of the flyback converter so that the stack as a whole can quickly and effectively respond to switching demand—storing electrical energy at a rate sufficient to keep drawing current from the mobile device at near the desired level when the primary coil 331 of flyback converter 320 is turned off and delivering stored energy to the primary coil (together with the draw current) when the primary coil is turned on.

In general, the number of capacitors used in the capacitor stack and the optimal capacitance values for the individual capacitors in the capacitor stack will vary based the nature of the flyback converter, the expected charging range of the capacitor and other design requirements. By way of example, in one specific application, a pair of capacitors having capacitances of approximately an order of magnitude difference (as for example, 4.7 µF and a 47 µF) are used in the capacitor stack—although again it should be appreciated that the optimal values for the capacitors may vary widely. Notably, the optimal capacitance characteristics of the transitory electrical energy store may vary based on factors such as the maximum primary coil current $I_{pri\_peak}$ and the voltage level of the discharge capacitor and therefore a variety of design choices may be made in the design of the transitory electrical energy store 305.

Figure 5B:
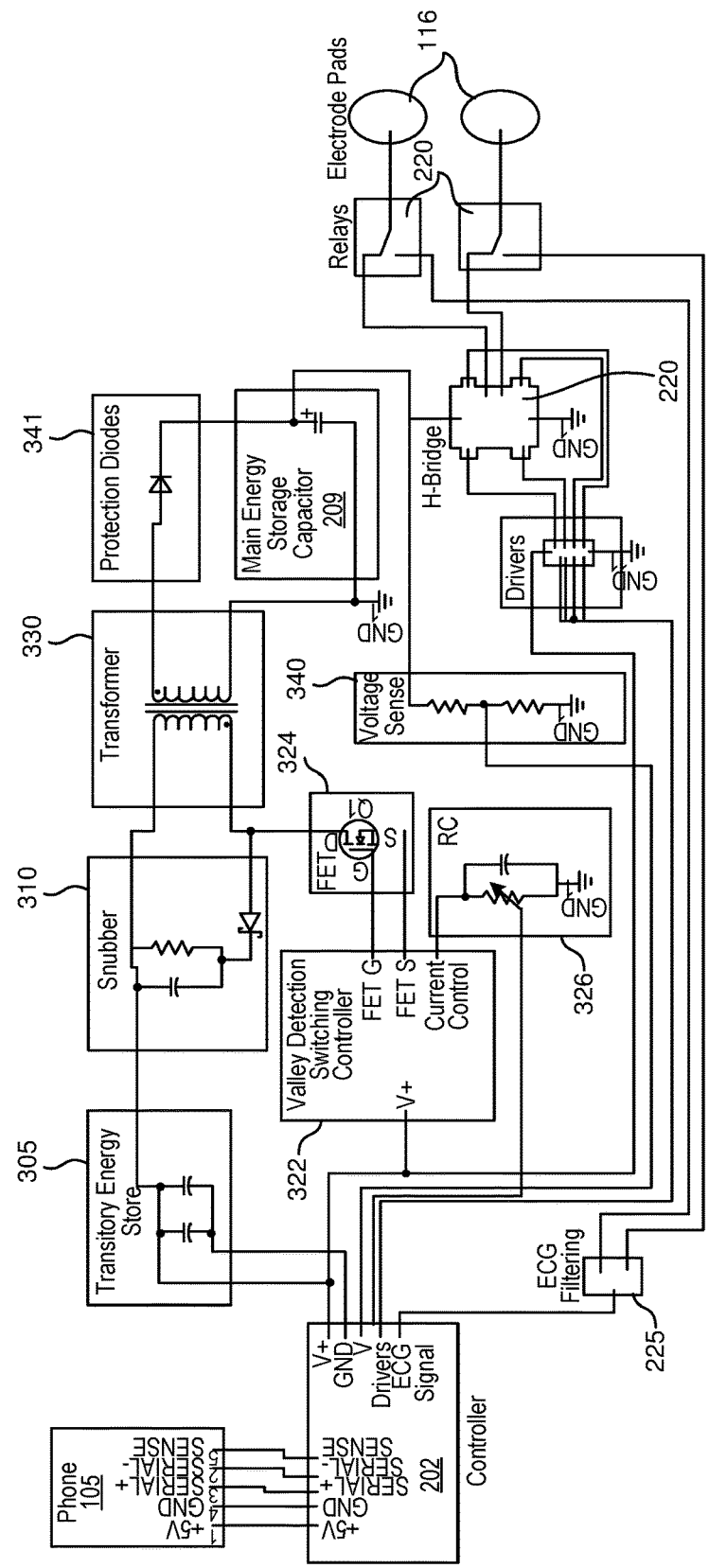
FIG. 5B is a schematic circuit diagram of an alternative defibrillator electronics architecture that utilizes the valley switching flyback converter of FIG. 5A.

Although a capacitor stack is illustrated in FIGS. 5A and 5B, in other embodiments the transitory electrical energy store may utilize one or more inductors with one or more capacitors (one example of which is shown in the digitally controlled current limiting Buck Converter of FIG. 3) or a wide variety of other electrical circuits may be utilized to form the transitory electrical energy store.

In many implementations the capacitors and/or inductors used in the transitory electrical energy store will be fixed and chosen based on overall design goals. However, in other implementations, the transitory electrical energy store 305 may have programmably variable capacitance and/or inductance characteristics. This can be accomplished, for example, by providing a bank of capacitors and a switching structure that allows individual capacitors to be selectively included or excluded from the active capacitor stack to thereby allow the capacitance of the transitory electrical energy store to be programmably varied. This arrangement has the advantage of allowing the capacitance characteristics of the transitory electrical energy store 305 to be varied based on factors such as the current delivery capabilities of the mobile device (power supply) the maximum primary coil current $I_{pri\_peak}$ and the then current voltage level of the discharge capacitor. With this arrangement, the capacitance characteristics of the transitory electrical energy store can be programmed before charging begins and updated as desired during charging to facilitate more efficient charging of the discharge capacitor 209. Of course, in other embodiments, the inductance of a component or both capacitance and inductance may be programmatically changed during charging to dynamically tune the charging circuit in a manner that improves charging efficiency.

FIG. 5B is a schematic diagram that illustrates an AED electronics architecture that utilizes the valley switching flyback converter of FIG. 5A. In this embodiment a smart phone or other mobile computing/communication device 105 is arranged to be coupled to defibrillator unit 110. In some embodiments, the smart phone may be coupled to the defibrillator unit using a removable connector cable such as a USB cable, a lightning connector cable or any other suitable removable plug in type cabling. In other embodiments, the mobile device 105 may be coupled to the defibrillator using more permanent wiring. In still other embodiments, the mobile device may be coupled to the defibrillator wirelessly—as for example using a short range wireless communication protocol for communications and inductive charging to facilitate the transfer of energy to the defibrillator unit to facilitate charging the discharge capacitor.

The defibrillator unit 110 includes defibrillator controller 202. Power received from the mobile device 105 powers the capacitor charging circuitry 300 which charges the main energy storage (discharge) capacitor 209. The capacitor charging circuitry in this embodiment includes transitory energy store 305, snubber 310, and transformer 330. The transformer is used in the valley detection flyback converter, which also includes valley detection switching controller 322, switch 324, and maximum transformer current control circuit 326. In some embodiments, the valley detection flyback converter may be a quasi-resonant flyback converter. A voltage sensor 340 is arranged to read the voltage of main energy storage capacitor 209 and provide that reading to defibrillator controller 202. Protective diodes 341 may be used to prevent current from flowing backwards from the capacitor 209 through the transformer 330.

The discharge circuitry includes H-bridge 220 along with the drivers 221 that drive the H-bridge switches. The drivers 221 are directed by defibrillator controller 202. The H-bridge 220 outputs a biphasic (or other multi-phasic) shock to patient electrode pads 116 through relays 229. The relays 229 are configured to switch between an ECG detection mode in which the patient electrode pads 116 are coupled to the ECG sensing circuitry 225, and a shock delivery mode in which the patient electrode pads 116 are connected to H-Bridge 220 to facilitate delivery of a defibrillation shock to the patient. Although specific components are represented in FIG. 5B, it should be appreciated that their respective functionalities may be provided by a variety of other circuits.

Figure 9:
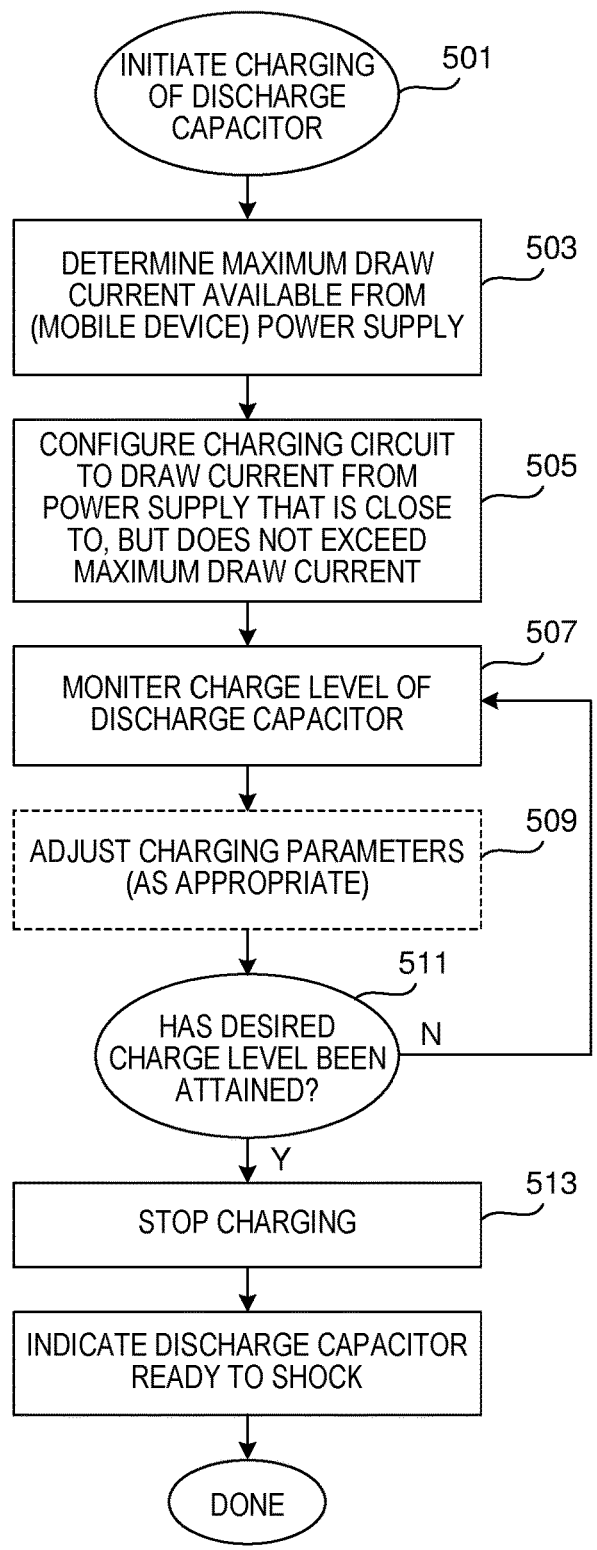
FIG. 9 is a flow chart illustrating a discharge capacitor charging scheme.

Referring next to FIG. 9, a variety of methods suitable for controlling the charging of the discharge capacitor 209 will be described. Initially, when a decision is made to initiate charging (step 501), the defibrillator controller 202 determines the maximum draw current that is available from the power supply (step 503). The decision to initiate charging can be made in a variety of ways. In general, it is desirable to automatically begin charging any time that it is likely that the defibrillator unit 110 may be utilized in an emergency situation. This can take the form of initiating charging as soon as the defibrillator unit is activated in a manner that suggests it might be used.

In some embodiments, charging automatically begins when a mobile device is initially connected to the defibrillator unit 110. This approach is particularly appropriate for stand-alone defibrillator units where a user is expected to plug the defibrillator unit into a mobile phone or other mobile device to facilitate use. In other embodiments, launching a defibrillation app, or a user inputted indication of an emergency or a desire to turn on, use or charge the defibrillator may initiate the charging. In still other embodiments, physical actions such as removing an end cap, or cover, pulling a tab or pressing a button can be used to initiate the charging. These latter approaches are particularly appropriate in embodiments in which a mobile device is already connected to the defibrillator unit 110 (as may occur when a mobile device is packaged together with the defibrillator unit, during training, or a variety of other circumstances) and in conjunction with the charging of the shock delivery capacitors in the context of more conventional defibrillator designs.

In some specific embodiments, the charging automatically begins when the defibrillator is initially activated or powered-on. Such activation can take a based on a manual input such as pressing an "on" or "activate" button, flipping an on/off switch to the "on" state, turning on a mobile communication device that is packaged as a part of the defibrillator (e.g., by pressing a home button or performing a gesture that activates the mobile communication device from a sleep, standby or otherwise low activity mode), removing an end cap or cover, pulling a tab or in other suitable manners. In such embodiments, the charging automatically begins when the user first does something that shows that they want to use the defibrillator rather than waiting to charge the capacitors until a shockable rhythm has been detected or a decision is made that delivering a shock is appropriate.

Charging (recharging) this discharge capacitor will also generally be automatically initiated after any discharge occurs. Of course, charging may be initiated in a variety of other circumstance, as for example as part of a testing protocol or in other appropriate circumstances.

In some embodiments, an app 108 on the mobile device is launched automatically when the defibrillator unit 110 is initially connected to a mobile device, and/or the app begins its initial communications with the defibrillator unit upon such connection. In other embodiments, the app is preloaded on the mobile device and launched upon a physical trigger from the defibrillator unit 110, such as a cover tab or end cap being removed. In still other embodiments, the app may launch on a user's phone when the phone detects that it is close to the defibrillator (e.g., using near field wireless communication or other appropriate technologies).

The app may be configured to automatically inform the defibrillator controller 202 of the current delivery capabilities of the connected mobile device as part of those initial communications. Alternatively, the app may inform the defibrillator controller 202 of the make and model of the connected mobile device, the type of connector used, and/or provide other appropriate identifying information, such that the defibrillator may utilize a lookup table or other suitable data structure on the defibrillator itself to determine the current delivery capabilities of the connected device based on such information. In other embodiments, the defibrillator controller 202 may send a request to the app or other suitable component of the mobile device requesting an identification of the device's current delivery capabilities, or requesting information such as the connector type in use, the make and model of the connected mobile device or other information that is suitable for determining the device's current delivery capabilities.

In still other embodiments, the defibrillator controller may be arranged to set the current draw at a designated default rate (e.g., just under 500 mA) when first activated and then communicate with the mobile device to determine its current delivery capabilities. If a higher current output is supported by the connected device, the current draw can then be adjusted to the higher rate. Regardless of the approach used, the defibrillator controller 202 determines the current delivery capabilities of the connected device as represented by step 503.

If the defibrillator controller is unable to determine the current delivery capabilities of the connected device for any reason, then a default value may be used. Typically, the default value would be the lowest current delivery capability that could reasonably be expected to supplied by the mobile device. By way of example, when USB-2.0 connectors are supported, the default may be set at 500 mA or a value slightly less than that, e.g., 490 mA. When only USB-3.0 or more advanced connectors are supported, then the default may be set at 900 mA or a value slightly less than that (e.g., 890 mA). Of course other defaults can be used as appropriate for any particular implementation.

In some embodiments, a dedicated mobile device may be provided together with the defibrillator unit. In such embodiments, the device's current delivery capabilities would be known and there would be no need to interrogate the device to determine its current delivery capability.

When the maximum draw current is known, defibrillator controller 202 configures the charging circuit so that the charging circuit draws current from the power supply (e.g., the mobile device) at a rate that is close to, but does not exceed the maximum draw current as illustrated by step 505. In the embodiment of FIG. 5A, this is accomplished by setting the value of variable resistor 327, which sets the maximum primary coil current $I_{pri\_peak}$—which in the context of the illustrated design, effectively dictates (sets) the draw current given that the other components are generally fixed. However, it should be appreciated that in other embodiments, the draw current may be set in a variety of different ways. For example, as suggested above, if the capacitance characteristics of the transitory electrical energy store 305 are not fixed, its capacitance characteristics can be set as desired based on the state of the other components (e.g., the maximum primary coil current $I_{pri\_peak}$ and/or the current charge status of the capacitor 209).

Once the draw current is set, charging begins and the defibrillator controller monitors the charge level of the discharge capacitor (step 507). In the embodiment of FIG. 5A, the voltage sensor 340 monitors the voltage stored in the capacitor which provides an indication of its charge level. The detected voltage level is sent to the defibrillator controller 202.

In some embodiments, the current drawn from the mobile device (or other power supply) may tend to vary as the capacitor charges. In such embodiments, it may be desirable to adjust the charging parameters appropriately during the charging so that the charging circuit continues to draw current at close to the maximum allowable draw current as represented by optional step 509—which helps speed the charging process without causing the mobile device to cut power to the defibrillator.

For example, in the embodiment of FIG. 5A, if the maximum primary coil current $I_{pri\_peak}$ is maintained at a fixed level, the draw current will decrease somewhat in a predictable manner as the capacitor charges. Therefore, the defibrillator controller 202 may be arranged to occasionally adjust the maximum primary coil current $I_{pri\_peak}$ as the capacitor charges in a manner that maintains the draw current at close to the designated maximum allowable draw current. In a simple implementation, a lookup table or other suitable data structure may be used to identify the appropriate values for the variable resistor 327 at different charge levels and the defibrillator controller can occasionally direct adjustment of the variable resistor in a manner that maintains close to the desired draw current. Of course, in other implementations, the specific parameter settings that are adjusted and/or the data structures or algorithms used to determine the desired settings may be varied as appropriate for such embodiments. By adjusting the charging parameters during the charging cycle, the discharge capacitor can be charged more rapidly without exceeding the maximum allowable draw current. For example, when the transitory electrical energy store has programmable capacitance characteristics, such capacitance characteristics may be adjusted during charging as well.

In general, charging continues until the desired charge level is attained as represented by decision box 511. When the desired charging level is attained, the charging is stopped (step 513) and the app is informed that the discharge capacitor is charged and available to deliver a shock if needed (step 515). At that point, charging can be discontinued until a new command is received to charge (or increase the charge of) the discharge capacitor 209.

In the embodiment illustrated in FIG. 5A, the flyback converter 320 has a single stage which boosts the 5V input voltage suitably for charging the discharge capacitor to the desired discharge voltage level (typically at least 1400 to 2000 volts). In other embodiments, multiple stage flyback converters may be used. For example, in a two stage flyback converter, a first stage may be used to boost the voltage from the input voltage (e.g. 5V or lower when applicable) to 12 volts (which is a common input voltage for defibrillators) and a second stage can be used to boost the voltage from approximately 12 volts to a level suitable for charging the discharge capacitor 209 to its desired operational voltage level. When desired, more than two stages can be used in a multi-stage flyback converters (or any other multi-stage voltage booster), and the specific intermediate voltage level(s) can be widely varied in accordance with design preferences.

In still other embodiments, different types of voltage boosters may be utilized in combination. For example, a DC-DC boost converter may be used in series with a flyback converter. In one specific example, a DC-DC boost converter may be use to boost the 5V input to 12V with the 12V input being fed to a flyback converter (which may have one or multiple stages) that boosts the voltage to the desired operational voltage for the discharge capacitor 209. In still other embodiments, other types of voltage boosters may be used alone or in combination with boost converters and/or flyback converters and the specific operational voltages of each voltage boosting component/stage may vary widely.

Figure 16:
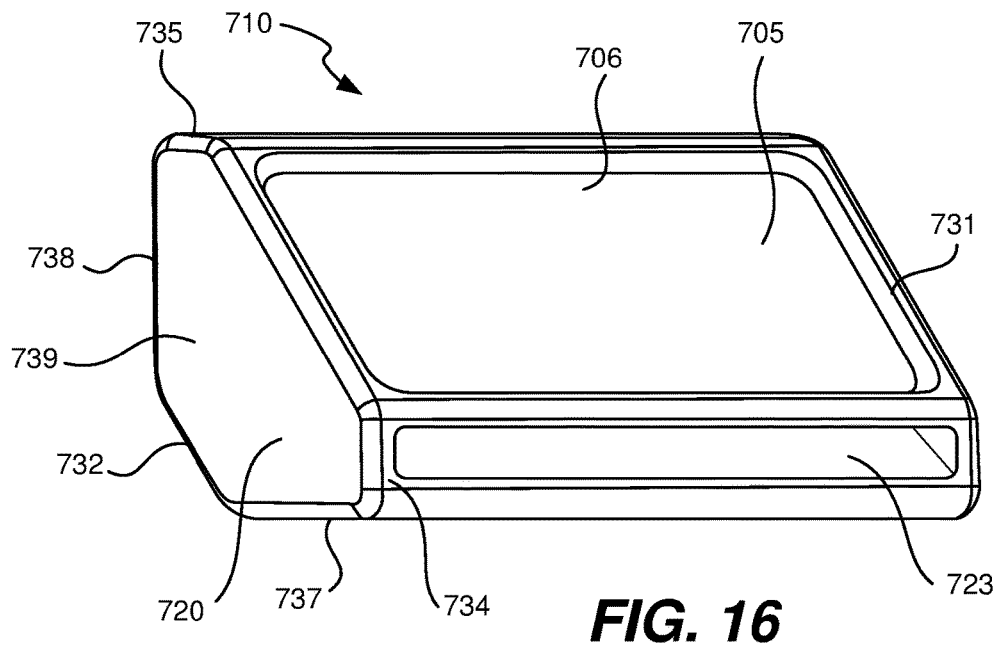
FIG. 16 is perspective view of another alternative defibrillator embodiment that includes an embedded smart phone.
Figure 17:
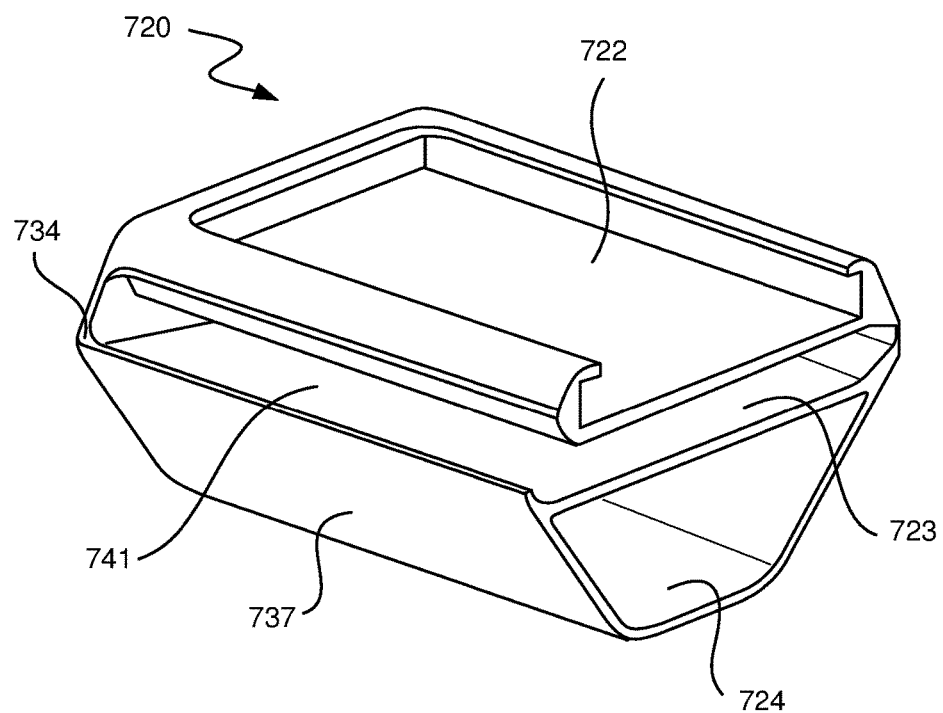
FIG. 17 is a perspective view of the housing of FIG. 16 alone with its end cap removed.
Figure 18:
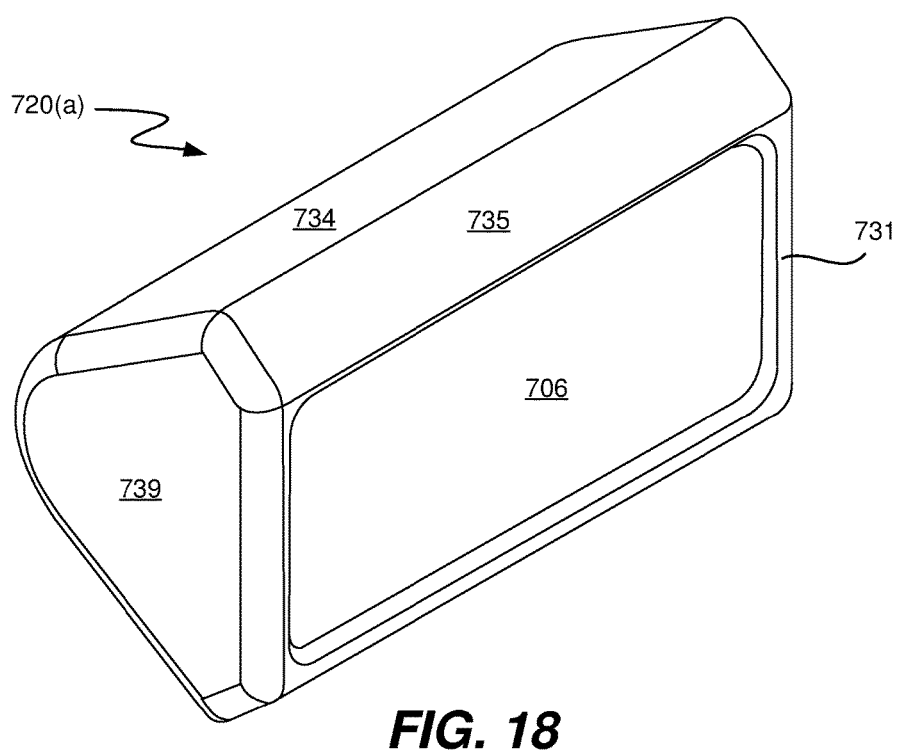
FIG. 18 is a perspective view of another alternative defibrillator embodiment that also includes an embedded smart phone.

Some of the primary described embodiments contemplate the use of an independent mobile device as the power supply for a defibrillator unit. However, it should be appreciated that many of the features of the described flyback converters and other aspects of the described capacitor charging circuits may be utilized in a wide variety of different defibrillator applications. By way of example, they may be used in conjunction with defibrillators having a dedicated mobile device packaged together therewith in a defibrillator housing (some examples of which are illustrated in FIGS. 16-18) that serves as the power supply; they may be used in conjunctions with defibrillators that obtain their power from external power supplies other than a mobile communication device; they may be used in conjunction with more standard defibrillator designs which have an integrated battery that is used to supply the power required to charge the shock delivery capacitor(s) and/or and integrated user interface; and they may be used in conjunction with a variety of other defibrillator designs, including manual defibrillators, wearable defibrillator, implantable defibrillators, etc. For example, the described valley switching aspects of the flyback converter may be incorporated into any defibrillator design that includes a flyback converter. Similarly, the variable maximum transformer primary coil current control approach, and/or updating the maximum primary coil current based on the capacitor's charge level can be incorporated into any defibrillator design that includes a transformer.

Discharge Circuit

The discharge capacitor 209 is coupled to a discharge circuit 220 that controls the delivery of a defibrillation shock. The defibrillator may be designed to deliver a monophasic shock, a biphasic shock or other multi-phasic shock or any other suitable waveform. As will be appreciated by those familiar with the art, biphasic shocks are currently preferred for medical reasons. Another advantage of biphasic shock delivery is that biphasic shock protocols typically require the delivery of less shock energy than monophasic shock protocols.

Figure 10:
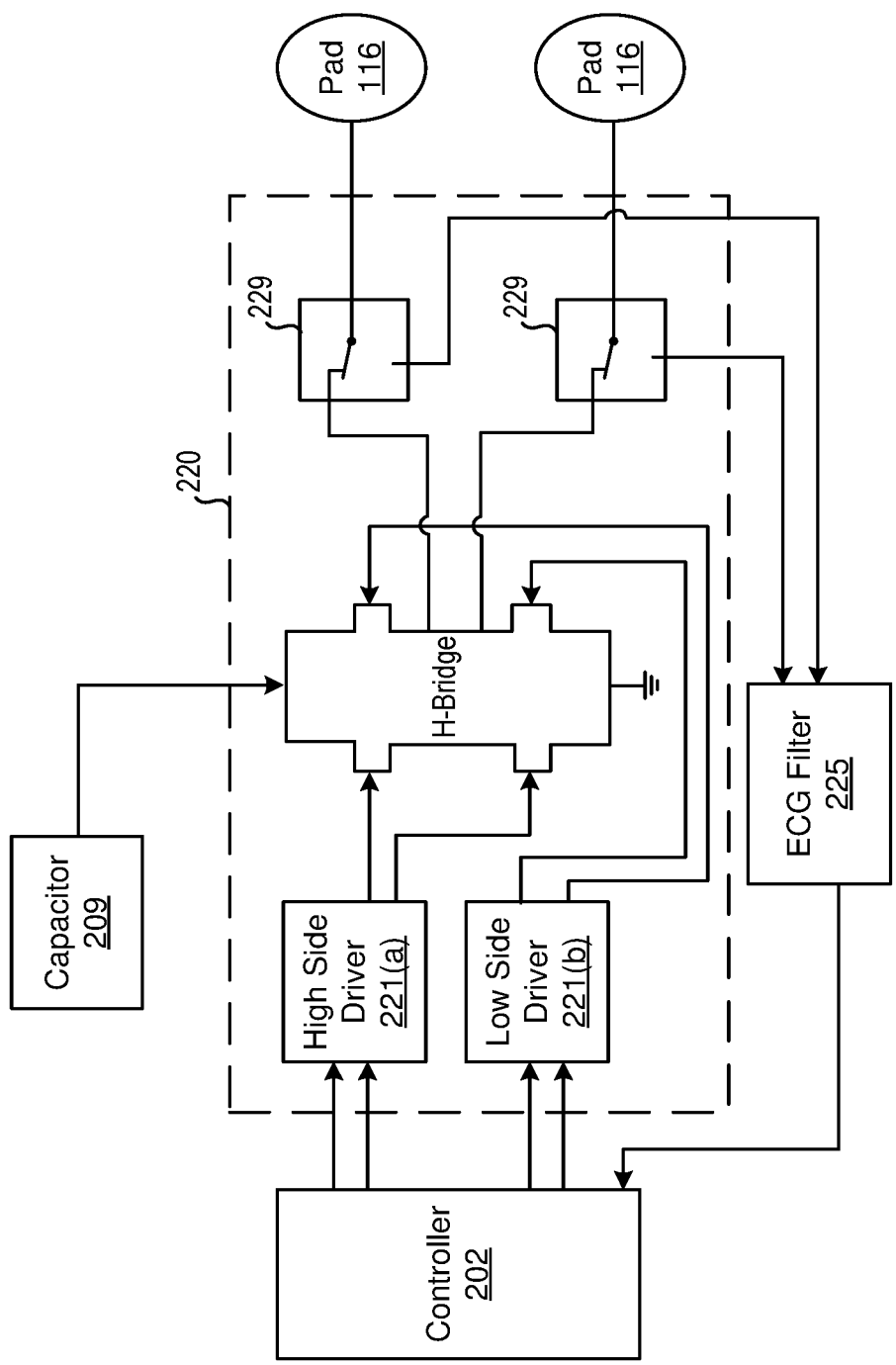
FIG. 10 is a schematic circuit diagram of a discharge circuit suitable for use in some of the described defibrillators.

One suitable biphasic shock delivery circuit 220 is illustrated in FIG. 10. The illustrated embodiment utilizes an H-bridge 220 discharge control circuit with high and low side drivers 221, so that the high voltage line can feed to either of the two AED pads 116 (this is what makes it biphasic). The activation, timing and safety checks of the discharge circuit 220 are controlled by defibrillation controller 202.

For a monophasic shock, an inductor/flyback diode (not shown) may be provided as the discharge control circuit 220 to make the capacitor discharge last 10-12 ms.

Of course the nature of the discharge circuit 220 can be varied to deliver any desired shock profile. When desired, more complex shock delivery circuitry may be utilized to provide greater control of the waveform of the delivered shock.

ECG Sensing

ECG sensing/filtering circuit 225 senses electrical activity of the patient's heart when the pads are attached to a patient. The filtered signal is then passed to defibrillator controller 202, which passes the signals on to the app 108 for analysis to determine whether the detected cardiac rhythm indicates a condition that is a candidate to be treated by the administration of an electrical shock (i.e., whether the rhythm is a shockable rhythm) and the nature of the recommended shock. The app then instructs the controller 202 when to deliver a shock and the nature of the desired shock. In alternative embodiments, the controller 202 can do the analysis of the ECG signals.

Offloading the ECG analysis to the mobile device 105 has several potential advantages. Initially, it simplifies the design of the defibrillator electronics and reduces the processing requirements on controller 202. Since the CPUs on conventional smart phones and tablet computers are quite powerful, they are very well suited for handling the ECG analysis. Furthermore, the ECG processing algorithms can readily be updated when appropriate using standard app updating protocols. Still further, the fact that the detected ECG rhythms and diagnoses are present on the mobile device make it very easy to share that information with first responders on site at the time of an incident or to transmit that information to medical personnel either during the incident (e.g. in a telemedicine setting) or after the incident. In defibrillators that have a manual operation mode, the ECG rhythms and shock history can be displayed to the EMT or other medical personnel to support the manual operation mode. When proper medical information handling procedures are followed, the ECGs and the shock history can also be shared with researchers to support medical research.

Since both the high voltage shock delivery and the low voltage ECG sensing require use of the defibrillator pads 116, both the discharge circuit and the ECG sensing circuit 225 are electrically coupled to the defibrillator pads 166 through relay(s) 229 which facilitates switching the pads 116 from the low voltage system (ECG reading) to the high voltage system (discharge). In the illustrated biphasic shock deliver system, each pad 116 may have an associated relay 229. The state of the relay(s) is/are controlled by controller 202. In the default state, the pads are preferably connected to a filtering ECG sensing/filtering circuit 225 (i.e., to the low voltage system) so that the patient's ECG can be read as soon as the pads are attached to the patient and at other times in the process, and so that in the event of a power failure, the relays default to a low voltage system for safety reasons. When delivery of a shock is desired, the controller 202 directs the relay(s) to switch to the high voltage discharge circuit 220. Once the relays are switched, the shock can be delivered. After the shock is delivered, the relay is preferably switched back to the low voltage (ECG sensing) system so that the patient's heart's response to the shock can be evaluated and the app can determine whether any additional shocks are advised.

In some embodiments, separate circuit boards are provided for the high and low voltage electrical systems. Although such a division of components is optional, it helps protect the sensitive low voltage electronics from the high currents and fields associated with the high voltage components and can help simplify any required or desired shielding. In a specific embodiment discussed below, the boards are longitudinally stacked within a housing 120 with the low voltage circuit board being located closer to the electrical connector compartment of housing 120 and the high voltage circuit board being located closer to the pad compartment. This allows for very efficient packaging in the housing, helps for shielding (preventing the low voltage electronics from being adversely affected by close proximity to high voltage traces), and helps with modularity in the electronics design. Because two end caps are provided (one for the connector cable and one for the pads), the low voltage components can very clearly be separated from the high voltage components. Low voltage components are on the connector cable side of the housing, whereas the high voltage components including the high voltage circuit board and the capacitor (which is the biggest volumetric component) and the pads are housed in the opposite side of the casing.

In one particular embodiment, the low voltage circuit board includes microprocessor 202, the current limiting circuit 205 and the ECG sensing/filtering circuit 225. The high voltage circuit board includes voltage booster 207, discharge control circuitry 220 and relays 229 and is coupled to capacitor 209. In other embodiments, all of the electrical components can be installed on a single board or packaged in a variety of other suitable manners.

Use of Additional Power Sources

In the embodiments described above, a single mobile device is used to provide the power to charge the discharge capacitor 209. It will be appreciated that the speed at which the discharge capacitor can be charged will be limited in significant part by the current delivery limitations of the mobile communication device that provides power to the defibrillator. This is due, in part, to the fact that most mobile communication devices and/or connector protocols impose limits on the current that can be drawn from the device. In some alternative embodiments, multiple power supplying devices can be used in parallel to charge the discharge capacitor 209. The other power supplying device(s) can be other mobile device(s) (e.g., mobile phones or tablet computers) or can be dedicated power supplies such as USB compatible power packs, power banks and battery packs that are becoming increasingly popular for usage as cell phone backup power accessories. In circumstances in which multiple mobile communication devices are connected, only one of the mobile communication devices would typically be used for control purposes, with the other essentially being utilized as additional power supplies.

An advantage of utilizing parallel devices as power supplies is that it can significantly reduce the time required to charge the discharge capacitor. By way of example, using two mobile devices in parallel as power supplies can cut the time required to charge the discharge capacitor 209 to any particular level nearly in half. To accommodate the use of multiple power supplies, more than one (as for example 2 or 3) connector cables 113 or a dongle type connector cable with multiple different source connector ends can be provided. With these arrangement, if multiple people are around at the time the defibrillator is used, any extra available phones or other suitable power supplies can be connected to speed the charging. An additional benefit is that if a large number of shocks are required for any reason, the battery capacity of the primary connected mobile device is less likely to become a limiting factor.

To that end, it is understood that portable AEDs are typically expected to have sufficient battery power to deliver multiple defibrillation shocks (which would often—but not necessarily always—be delivered at two minutes intervals at sequentially increasing intensities). Some regulatory standards suggest the ability to deliver on the order of 15 or more shocks. In practice, it is relatively rare that more than 5 or 6 shocks would be applied in any one incident and four or less shocks is understood to be most common. Most cellular smart phones (and other suitable mobile communication devices) are capable of supplying such energy levels without excessively draining their batteries. For example, in practice, charging the defibrillator for one 150 J discharge tends to drain under 2% of the charge from most currently popular smart phones. Therefore, most cellular smart phones would be able to deliver the electrical energy required to provide a number of shocks. The ability to deliver numerous shocks can be even further enhanced by embodiments that have the ability to simultaneously obtain power from more than one source.

While it is contemplated that multiple mobile communication devices may be used to speed the charging, it should be appreciated that some people carry spare power supplies or various other electronic devices that may be capable of delivering power through standard electrical cables such as various USB cables, microUSB cables, lightning cables, etc. To the extent that any such devices are available at the time of use, they can be used as supplemental power to speed the charging process when multiple connector cables 113 are provided. Any connected device that has the appropriate processing power (as for example other mobile communication devices, notebook computers, etc.) can also assist with or perform any of the required processing or control.

The defibrillator unit 110 is also preferably configured so that the connected mobile device can be swapped out in the middle of a treatment if necessary. This can be desirable in the event that the initial phone used had a low charge level and can no longer be used for charging. In order to facilitate switching of the connected mobile device, the controller 202 can optionally be configured to store the current defibrillator state and to inform a newly connected device of that state (including any diagnoses that have been made by the preceding device) when the new device is connected. In this manner, the second connected device can pick up where the first one left off. In other embodiments, such information can be transferred wirelessly between the devices (using, for example, Near-field communications (NFC), Bluetooth, or short distance wireless communication protocol. In still other embodiments, such information can be transmitted from the first device to the cloud and from the cloud to the second device to accomplish the same function. Alternatively, the newly connected device can very quickly go through a series of status checks itself to determine the current state of the event—again appearing to pick up where the first device left off.

In yet other embodiments, the defibrillator unit 110 may include a relatively small battery or supercapacitor that can be used to supplement power provided by the mobile device—or vice versa, the mobile device can supplement the power of the on-board energy storage device. In some embodiments, the supplemental power supply is rechargeable so that it can be recharged if its charge drains somewhat after prolonged storage. A potential advantage of providing such a supplemental power supply is that it can be used in parallel with power from the connected mobile device to speed the charge time. In some applications this may be desirable particularly in connection with the initial charging of the discharge capacitor. This is because the initial charge is typically the most time critical shock, because it may be desirable to deliver the first shock shortly after it is determined that the patient has a shockable heart rhythm. Most shock protocols contemplate a relatively extended period between shocks (e.g. 2 minutes) in circumstances in which subsequent shocks are required—which provides plenty of time to recharge the discharge capacitor.

When the defibrillator has supplemental power a variety of different power management schemes can be used based on the relative charge levels of the mobile device vs. the supplemental power supply. For example, in some applications, the defibrillator controller 202 or the app 108 can check the charge level of the mobile device by simply requesting the charge level. If the battery on the mobile device is low, power can be drawn solely from the supplemental power supply. Similarly, if a cell phone is incapable of delivering power for any reason, the power to charge the defibrillator can again be drawn from the supplemental power supply. Alternatively, if both the supplemental power supply and the connected mobile device have a high battery charge level, power can be drawn from both to speed the charge. If the supplemental power supply is low for any reason, then power can be drawn exclusively or primarily from the connected mobile device—and if desired, power from the mobile device can further be used to charge the supplemental battery in times when its power is not needed to charge the discharge capacitor.

Alternative Capacitor Configurations

In most of the embodiments described above, a single discharge capacitor 209 is typically used. However, in other embodiments, multiple discharge capacitors may be used with minimal changes to the other circuitry. For example, in some embodiments, a plurality of lower voltage capacitors, may be arranged in parallel for charging and then switched to be arranged in series for discharge. For example, a group of four or five 600 volt capacitors may be arranged to be charged in parallel, and then switched to an electrical series configuration after the charging is complete to facilitate a higher voltage discharge. An advantage of this approach is that charging at lower voltages tends to be more efficient so that the charging occurs more rapidly. A disadvantage of this approach is the more extensive switching and discharge control is required.

In another embodiment, a plurality of lower voltage capacitors may be arranged in series or arranged in parallel for both charging and discharging. For example, a group of four or five 600 V capacitors may be arranged in series. An advantage of this approach is possible cost and size savings that may be achievable with lower energy capacitors.

In another embodiment, a pair of capacitors or capacitor units having opposite polarities may each be charged to a level suitable for delivering half the total shock energy requirements. One of the capacitors is configured to discharge through a first one of the defibrillator pads and the other is configured to discharge through a second defibrillator pad. In yet another alternative, two capacitors having opposite polarity can be configured to discharge through the same defibrillator pad, with the other defibrillator pad always being tied to ground. With this arrangement, current flows from the positively charged capacitor to the grounded defibrillation pad to form the first phase of a biphasic waveform when the first capacitor is discharged, and current flows from the grounded defibrillation pad to the negatively charged capacitor to form the second phase of a biphasic waveform when the second capacitor is discharged.

Figure 11A:
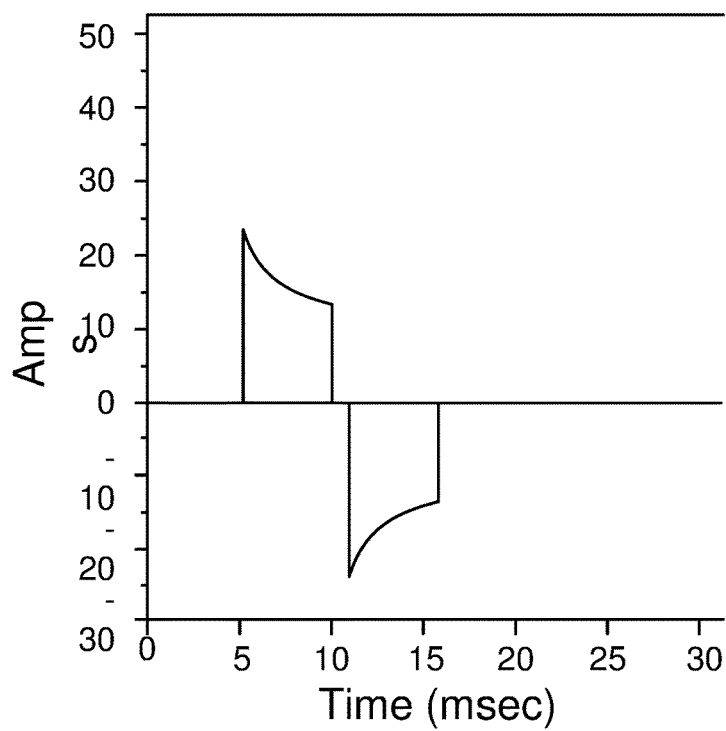
FIG. 11A is a graph illustrating a representative shock waveform generated by a pair of equally sized, oppositely polarized discharge capacitors in accordance with another embodiment.

These arrangements have the potential to provide a biphasic shock that has a somewhat different waveform than conventional biphasic shocks. For example, as best seen in FIG. 11A, each phase has approximately the same energy level and the waveforms have the same magnitude but opposite polarities. This differs from conventional biphasic shocks in which the first phase tends to be delivered at a much higher voltage than the second phase—as seen, for example, if FIG. 11B which illustrates representative biphasic 150 J waveforms at three different patient resistance values.

In other implementations, the opposite polarity capacitors can be charged to different voltage levels and/or can be different sizes to facilitate further control of the energy dispatched during each phase. This gives even greater control of the nature of the different phases. For example, one of the capacitors can be charged to first level (e.g., 1200 volts) while the other is charged to a second level (e.g. 1000 volts) to facilitate biphasic shocks in which one of the phases discharges more energy than the other. The defibrillator controller 202 has complete control of which capacitor is charged to which level and the order in which the capacitors are discharged. Thus, the higher voltage capacitor can be discharged as either the first or second phase of the biphasic shock.

Figure 12:
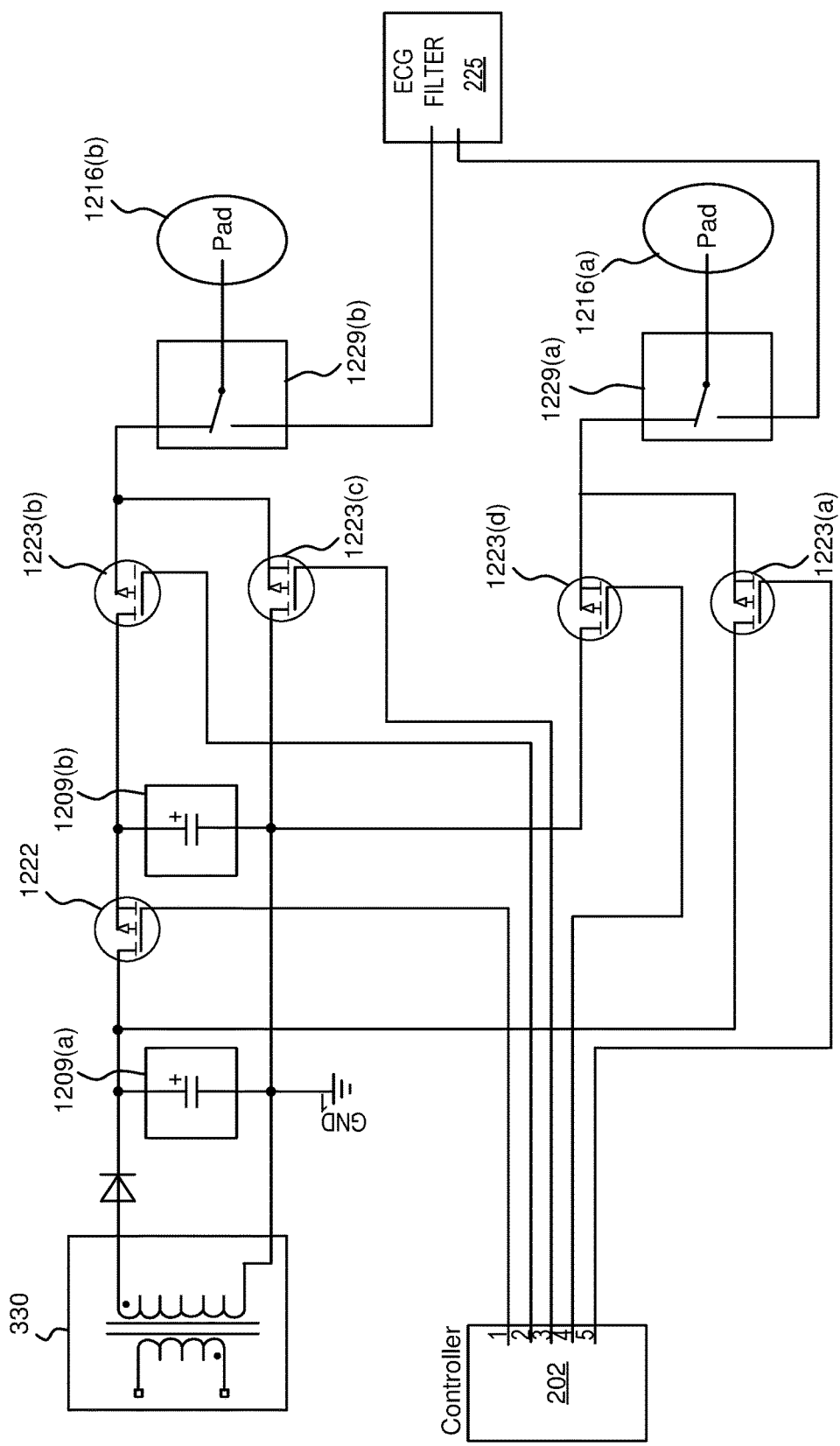
FIG. 12 illustrates a discharge circuit suitable for use with oppositely polarity capacitors.

FIG. 12 illustrates a representative discharge circuit that may be used to discharge a pair of capacitors 1209(a) and 1209(b) in opposite polarity. In this embodiment, the capacitors 1209(a) and 1209(b) are charged in parallel. To facilitate charging, a charging control switch 1222 is turned on by controller 202. This allows the capacitors 1209(a) and 1209(b) to be charged in parallel by the capacitor charging circuitry (such as any of the charging circuitry described above). Once the capacitors are charged, the charging is disabled by the controller 202 so that charging no longer occurs, and switch 1222 is turned off. When switch 1222 is turned off, the capacitors 1209(a) and 1209(b) are electrically isolated from one another which allows the capacitors to be discharged separately.

In the embodiment illustrated in FIG. 12, the discharge circuit is composed primarily of a set of four switches 1223(a)-(d) which are controlled by defibrillator controller 202. The positive sides of capacitors 1209(a) and 1209(b) are respectively coupled to different switches 1223(a) and 1223(b). Switches 1223(a) and 1223(b), in turn, are connected to relays 1229(a) and 1229(b), which, are each connected to an associated one of the defibrillator pad 1216(a), 1216(b). The ground sides of capacitors 1209(a) and 1209(b) are also connected to the relays, with the ground side of capacitor 1209(a) being connected to relay 1229(b) through a third switch 1223(c) and the ground side of capacitor 1209(b) being connected to relay 1229(a) through a fourth switch 1223(d). With this arrangement, a first phase of a defibrillation shock may be delivered by turning on switches 1223(b) and 1223(d) when the relays 1229(a) and 1229(b) are in discharge mode (i.e., switched to the discharge circuit). This causes high voltage current to flow from capacitor 1209(b) through switch 1223(b) and relay 1229(b) to pad 1216(b). In this state, the other defibrillator pad 1216(a) is connected to the ground through switch 1223(d). This discharge can be terminated at any time by turning switch 1223(b) off. After the first phase has been terminated, an opposite polarity shock phase can be delivered by turning on switch 1223(c) (which connects pad 1216(b) to ground), turning switch 1223(d) off (which disconnects pad 1216(a) from ground) and thereafter turning on switch 1223(a) (which connects pad 1216(a) to the high voltage side of capacitor 1209(a)). With this arrangement, high voltage current flows from capacitor 1209(a) through switch 1223 (a) and relay 1229(a) to pad 1216(a). The opposite polarity shock phase can be terminated at any time by turning switches 1223(a) back off. The on/off state of the various switches 1223 may be set by the defibrillator controller 202—although it should be appreciated that a separate discharge controller may be used in other embodiments.

With the described arrangement, a controlled biphasic shock can readily be delivered by turning the switches on and off appropriately. It should also be apparent that additional multi-phasic shocks having more than two phases can readily be provided using the same approach by simply turning the various switches 1223(a-d) back on and off appropriately. It should be noted that the discharge circuitry for this embodiment is simplified relative to the discharge circuitry used to deliver a biphasic shock waveform using an H-Bridge structure—with the switching control being simple enough that it can readily be controlled by the defibrillator controller 202 without requiring a separate discharge controller (although a separate discharge controller may be utilized when desired).

The switches 1222 and 1223 are preferably power switches capable of handling the high voltage/high power shock surges associated with the delivery of a defibrillation shock. By way of example power field effect transistors (FETs such as those shown in FIG. 12) or insulated-gate bipolar transistors (IGBTs) work well, although other switching structures may be used in other embodiments.

Dynamic Discharge Impedance Detection

Figure 11B:
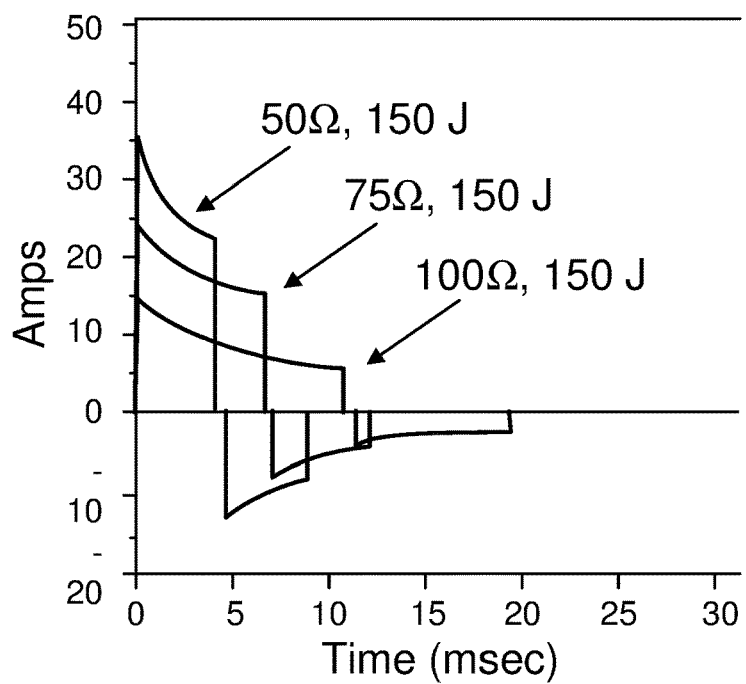
FIG. 11B is a graph illustrating potential target waveforms for delivering a 150 Joule biphasic shock in patients having 50, 75 and 100 ohm resistances respectively between the pads.

As is well understood in the art, different patients have different impedances in general, and the resistance/impedance observed between the defibrillation pads will vary based on pad placement as well. Therefore, many defibrillators measure the actual resistance or impedance between the pads prior to delivering a shock and then adjust selected shock delivery parameters accordingly to ensure that an acceptable shock waveform is delivered. For example, in the context of the delivery of a biphasic shock, when the patient resistance/impedance is known prior to delivering a shock, the discharge period for the first and second phases (sometimes referred to a the first and second pulses of the defibrillation shock) may be adjusted prior to delivering the shock so that each of the shock waveform phases imparts a desired energy level. By way of example, FIG. 11B illustrates potential target waveforms for delivering a 150 Joule biphasic shock in patients having 50, 75 and 100 ohm resistances respectively between the pads. The amount of energy delivered in the first phase of each shock is the same in each case. Similarly, the amount of energy delivered in the second phase of each shock is the same in each case. As can be seen, the discharge periods are different with the discharge periods generally being longer (and the shock voltages lower) for higher impedance patients. Thus, it should be apparent that when the impedance of the patient is known, the amount of energy delivered in each shock phase can be controlled (set) by adjusting the duration of the respective discharge periods.

Although measuring the patient resistance/impedance before commanding a shock works well, if the impedance of the shock delivery path or patient changes for any reason after the measurement has been made, but before the shock is delivered (or while the shock is being delivered), the actual energy level delivered in each of the respective phases may vary from the target levels.

Next, an alternative approach to controlling the energy delivered during each phase of a biphasic shock will be described. In this embodiment, the resistance between the pads is effectively detected during the delivery of the shock, and the period of the respective phases is determined "on the fly" during the shock delivery. This provides good control of the energy delivered during each phase.

In general, the discharge capacitor 209 will have a discharge characteristic (typically a generally exponential decay) which for any given charge level, varies primarily as a function of the patient resistance/impedance. The greater the patient impedance, the lower the shock current, which means that less energy is imparted by the shock in a designated period of time. For any given charge level and shock delivery impedance (which includes the patient impedance), the resulting shock waveform can readily be modeled In a specific embodiment, the capacitor voltage prior to discharge is known and the capacitor voltage is read again at a designated time after shock delivery has begun, as for example at 2 milliseconds into the shock delivery. With the knowledge of the starting capacitor voltage and the capacitor voltage detected at the designated mid-shock voltage reading time, the shock delivery impedance, the power delivered and the delivery waveform can be inferred. Since the power delivery waveform can be inferred, the period that is required to deliver any desired amount of energy can be readily determined. Therefore, if the design goal is to deliver X joules of energy during the first discharge phase of a shock, then the time at which the H-bridge should be switched to meet that design goal can readily be determined based on that initial mid-shock capacitor voltage reading. Thus, a multi-dimensional lookup table or other suitable data structure or construct can be used to correlate the mid-shock voltage reading to the H-bridge switching time(s) that are appropriate for delivering the desired shock. By way of example, one index for the multi-dimensional lookup table can be the charge level of the capacitor, and a second index for the lookup table can be the voltage detected at the designated mid-shock voltage reading. Each entry in the table can identify the switching time(s) for the H-bridge in the shock delivery circuit. That can include the timing for turning off the first phase, turning on the second phase, and turning off the second phase. Of course, not all of these values are required as they can readily be inferred based on the timing of the initial switching and other parameters values may be used to facilitate determination of the desired switching times.

This described approach effectively allows the shock delivery impedance (which includes the patient impedance) to be determined dynamically during shock delivery which allows the waveform to by adjusted on the go during the shock. Having said that, it should be appreciated that in many implementations it will not be necessary to explicitly determine the shock delivery impedance. Rather, the timing of the termination of the first shock pulse and the timing of any following pulses in a multi-phasic shock waveform can often be determined directly without explicitly calculating or otherwise determining the shock delivery impedance.

Effectively determining the shock delivery impedance on the fly also reduces or potentially eliminates the need to accurately measure the patient impedance prior to shock delivery—and especially immediately prior to a shock, which can delay the shock delivery by a small amount and, as a practical matter, compensates for any impedance variations that could potentially occur between impedance reading and shock delivery. In some embodiments, a patient impedance measurement that is taken prior to initiation of a defibrillation shock can be used to initially estimate a desired shock duration/timing and the mid-shock reading can be used to update the desired shock duration/timing as appropriate.

In some embodiments, two or more sequential capacitor voltage readings may be made which can be used to even further improve the estimate of the energy delivered during each phase and the control of the timing of the shock phase delivery. Such readings can also be stored and used as desired in reporting the nature of the shock delivered, etc.

The voltage sensor used for the mid-shock voltage reading can be the same voltage sensor used to monitor the voltage level of the discharge capacitor 209 as it is charged—e.g., voltage sensor 211 in the embodiment of FIG. 3, or the voltage sensor 340 in the embodiment of FIG. 5A. The voltage is read by defibrillator controller 202, which determines the desired H-bridge switching times and directs the internal H-Bridge switching accordingly. When shock discharge control systems other than an H-Bridge are used, the defibrillator controller can set the timing of the appropriate discharge switches accordingly.

Referring next to the flow chart of FIG. 19, a representative shock discharge control approach that utilizes dynamic shock pulse timing determination will be described. Although not shown in the flow chart, the patient impedance may be measured pre-shock at any time after the defibrillator pads have been attached using conventional techniques. When desired, that initial impedance measurement can be used to determine a desired charging level for the discharge capacitor and/or to estimate a desired shock timing. In the context of a biphasic shock that would include the desired duration and separation of the two shock pulses that make up the distinct, opposite polarity, phases of the biphasic shock.

Figure 19:
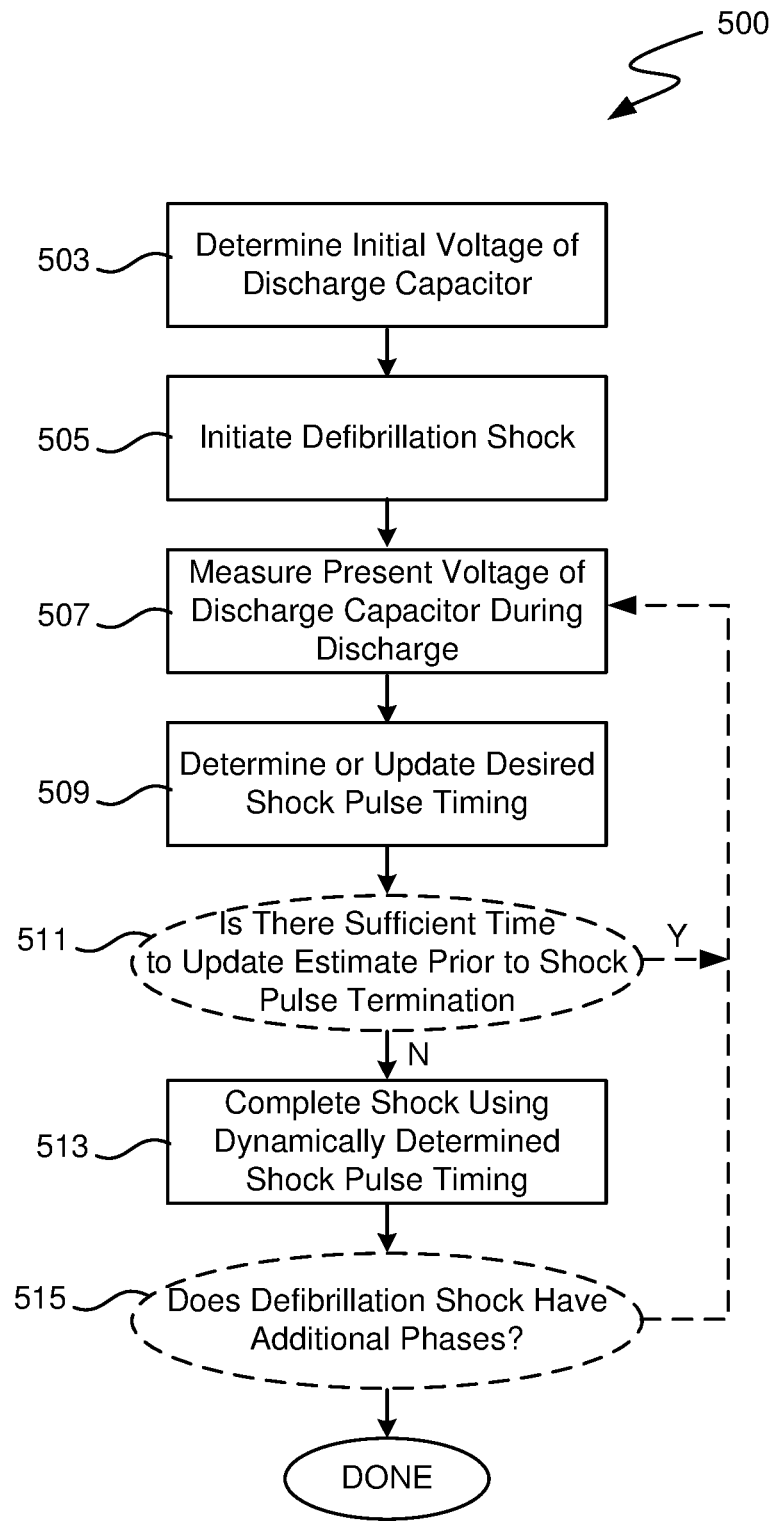
FIG. 19 is a flow chart illustrating a shock discharge control approach that utilizes dynamic shock pulse timing determination.

Referring now to FIG. 19, when it is time to deliver the shock, the initial voltage of the discharge capacitor is determined as represented by block 503. The capacitor voltage (which corresponds to a particular charge level) may be determined be reading a capacitor voltage sensor (e.g. voltage sensor 211) or in any other appropriate way. In many circumstances, the capacitor voltage may already be known to the defibrillator controller, which may be configured to read the capacitor voltage on a regular periodic basis.

When conditions are appropriate, the shock is initiated as represented by block 505. The shock may be initiated automatically by the defibrillator controller or an app on the mobile device, or it may be initiated in response to a shock command inputted by a user or any other appropriate shock command In general, the pads 116 are connected to the pads in a first polarity. When a monophasic shock is delivered, a single shock pulse is delivered with the pads connected in the first polarity. When a biphasic shock is delivered, the first phase of the shock (e.g., the first pulse) is delivered with the pads connected in the first polarity and then the polarity of the connection is switched to facilitate delivery of the second phase (e.g., the second pulse).

A short period after the discharge has begun, a then present voltage of the capacitor is read/measured as represented by block 507. Typically, the time at which the capacitor voltage is read will be predetermined, as for example 2 msec after the discharge begins, although the specific timing may vary and a fixed period is not strictly required in all implementations. Preferably the capacitor voltage is read quickly enough so that the capacitor won't discharge more than desired before the voltage is read, but after enough time has elapsed to be able to accurately predict the discharge curve.

As discussed above, this mid-discharge voltage reading is then used to determine or update the desired shock timing as represented by block 509. When a monophasic discharge is utilized, the shock timing determined will include the timing at which the discharge will be terminated. When a biphasic or more extended multiphasic discharge is contemplated, then the determined shock timing may also include the start and stop timing for the other shock phases as well. In some circumstances, the timing determined may actually update an estimated timing that is based on a pre-shock impedance measurement, a default shock timing or other appropriate shock timing setting. The shock timing may be determined algorithmically, through the use of look-up tables or other suitable data structures or using any other appropriate approach.

In some implementations/circumstances it will be desirable to check and/or update the shock timing multiple times during the shock delivery as represented by optional block 511. For example, voltage readings may be made every 2 msec or at other appropriate intervals and the shock timing may be verified or updated as appropriate each time that a reading is made—effectively repeating steps 507 and 509. This can be particularly desirable since it may be possible to better estimate the discharge characteristics and thus the desired pulse timing later in the discharge cycle. However, it is undesirable to wait too long to make the first estimate so that the first shock pulse doesn't extend longer than desired in circumstances in which the patient impedance is relatively low. It should be appreciated that these supplemental checks are optional and may be eliminated in some embodiments.

With the desired shock timing known, a switch may be turned off to disconnect the defibrillator pads 116 from the discharge capacitor 209 at the desired timing to complete the first shock pulse as represented by block 513. When a biphasic shock waveform is desired, the pads may then be electrically reconnected to the discharge capacitor after any desired or required switching interval and the second phase initiated at the desired timing. The pads are then electrically disconnected from the discharge capacitor 209 when the second phase is completed.

In some embodiments it may be desirable to utilize capacitor voltage measurements read during the second phase of a biphasic waveform in control of the duration of the second phase. In such circumstances the voltage of the capacitor may be read at specified times during delivery of the second phase of the shock waveform and the desired pulse timing may be updated accordingly as represented by optional block 515 which returns the logic from to step 507. Of course, the same approach can be used in the control of even further phases if a multiphasic waveform having more than two phases is used.

In some embodiments, separate capacitors may be used to deliver the first and second phases of a biphasic shock. In such embodiments, the described shock pulse width control approach can be used separately in the control of the pulses delivered by each capacitor. One such discharge capacitor architecture is described above with respect to FIG. 10. However, it should be appreciated that the described shock pulse control approach can be used in conjunction with virtually any capacitor architecture.

Use Scenarios

In the primary described embodiments, the defibrillator capacitor 209 is charged from the phone when the AED is deployed. Although this is expected to be one of the primary use scenarios, other use scenarios can be supported as well. For example, if the user will be attending a particular event at which they are particularly concerned about the risk of someone having a cardiac arrest incident, they could proactively charge the AED prior to the event. The availability of this potential use mode depends on the rate at which a defibrillation charge stored in high voltage capacitor 209 dissipates when no shock is delivered.

In practice, the AED can be configured to passively dissipate the capacitor charge over any time period desired. In some applications, it may be desirable to passively dissipate the charge over a relatively short period of several hours or less which has the potential advantage of reducing the risk of a shock being inadvertently delivered through misuse of the device. In other applications, the AED can be configured to passively discharge the capacitor over a longer period such as 3-4 days.

As discussed above, a capacitor voltage sensing circuit 211, 340 (such as voltage divider) is provided to facilitate monitoring the state of the capacitor charge. The sensing circuit will draw a small amount of current from the capacitor and thus, when the sensing circuit is connected to the capacitor, it provides a small drain on the capacitor charge, thereby acting as a capacitor charge bleed circuit. The time period over which the capacitor dissipates its electrical charge through the voltage sensing circuit can be controlled by varying the size of the voltage sensing circuit's equivalent resistance. For example, if a several hundred mega-ohm resistor is used as the voltage sensing circuit resistor, the defibrillation capacitor charge will dissipate over a time frame on the order of 3-4 days which facilitates the pre-charging use mode. If longer charge holding periods are desired, a switch (not shown) can be provided to allow controller 202 to turn off the voltage sensing circuit 211, 340, which eliminates the voltage sensing circuit drain and prolongs the charge hold time. If shorter passive discharge periods are desired, either a smaller voltage sensing circuit resistor can be used or a separate discharge circuit (active or passive) may be provided.

In other embodiments, a high resistance resistor can alternatively or additionally be provided between the leads of the capacitor to form a constant and permanent bleed. Alternatively, a mechanism may be provided for internally discharging a charged capacitor if a shock is not required after the shock discharge capacitor has been charged. Such a mechanism can take the form of a power resistor or a bank of power resistors that are designed to receive a monophasic or biphasic shock. Such a discharge mechanism can also be used for performing self-checks of the discharge functionality.

As pointed out above, one desirable way to use the defibrillator units described above is to connect an operator's personal smart phone (or other personal mobile communication device) to the unit at the time of an incident thereby: 1) powering the defibrillator unit from the phone; 2) using an app installed on the phone as a user interface; 3) using the processing power of the phone to handle certain processing and control tasks associated with the use of the defibrillator; and 4) provide connectivity that can provide a variety of support services. In other implementations, the integrated smart phone may be connected using wireless inductive charging and a short range communication protocol as previously described.

In other applications, a custom built smart phone or other mobile computing device can be packaged together with the defibrillator unit so that the operator does not have to use their own phone. This works well because most smart phones today (including low cost smart phones) package a number of features that are very useful in defibrillator control and cardiac arrest incident management into a very small package. For example, most smart phones have significantly more processing power than conventional defibrillators. They have a high quality display and audio capabilities that can be leveraged to guide a lay or minimally trained operator through an incident. They can provide a user interface that potential users are very familiar with, which may reduce a lay user's reluctance to try to operate a life saving medical device that they are not particularly familiar with in an emergency situation. They include integrated batteries that provide more than enough power to power a defibrillator. They have built in communication technologies such as cellular, Wi-Fi and Bluetooth capabilities that can be used to facilitate a variety of response related services. They also have built in sensor such as audio microphones, cameras, etc. that can be use in advantageous ways during a medical incident.

In some implementations the integrated smart phone (or tablet or other mobile device) may be permanently attached to the defibrillator housing or fixedly wired to the defibrillator unit. In other implementations, connecting cables can be provided (e.g. packaged internal to the housing) as described in the context of defibrillators suitable for use with an operator's personal smart phone or other mobile device.

Another feature supported by the use of a mobile device is the availability of an established infrastructure for readily and easily updating software remotely. As should be apparent, the defibrillator app can be arranged to define the amount of energy that is delivered in each shock phase. Therefore, the nature and waveform of the shock can readily be modified through software (app) updates to reflect the latest medical research and shock protocol recommendations. This can include using different types of waveforms for different types of detected heart rhythms, using different energy discharge levels based on patient impedance or other factors, or otherwise programmably varying the shock profile based on general medical recommendations or medical recommendations based on any detected patient characteristic.

The Defibrillator Unit Housing

The defibrillator unit 110 includes a housing 120 that encases the electrical components of the defibrillator. The housing unit may take a wide variety of different forms. By way of example, U.S. Provisional Patent Application Nos. 62/433,067 filed on Dec. 12, 2016 and 62/566,896, filed Oct. 2, 2017, each of which is incorporated herein by reference in its entirety, describe some suitable housing structures.

Figure 14:
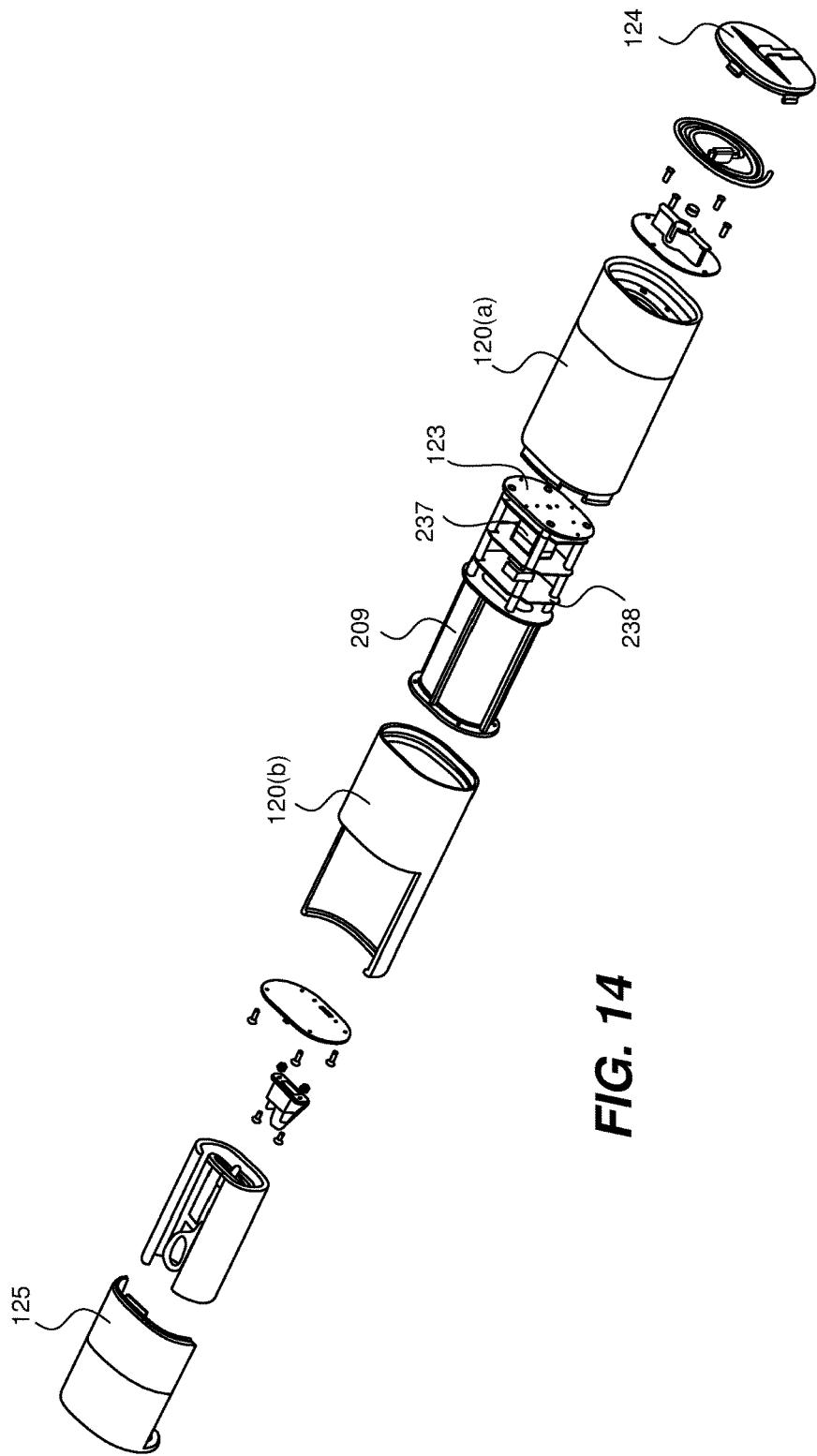
FIG. 14 is an exploded view of the defibrillator illustrated in FIG. 1.

Referring next to FIGS. 1 and 14, one particular housing embodiment will be described. In the illustrated embodiment, housing 120 is generally tubular with a generally oval shaped cross sectional geometry. The opposing ends of the housing 120 have large end openings 121, 122 that are covered by associated end caps 124, 125. The oval shaped housing has two flat, parallel sides thereby creating a "stadium" shaped oval cross section. This oval shaped tubular housing provides a familiar feel to users and is easy to carry in a backpack, a sports bag, a hand bag or purse, the glove compartment of a car or in any of a wide variety of other manners thereby making the defibrillator unit highly portable. The flat sides help prevent the unit from rolling.

In this embodiment, one end of the housing 120 forms a compartment that holds the connector cable 113 that plugs into the phone. The other end forms a compartment (sometimes referred to herein as a drawer) that holds the defibrillator pads 116. The drawer may also optionally contain a small pair of scissors to assist in cutting away clothing if necessary, wipes, a small razor to shave off patient hair in the regions where defibrillator pads 116 are to be attached and/or a mouth protection device for a user administering CPR.

The exterior of the housing 120 is screwless and completely watertight, allowing the AED to be transported, and if necessary used, in a variety of weather conditions. Internal clipping mechanisms and o-rings are used to secure and insulate the interior. Gaskets are used to further insulate the electrical components inside when the caps are taken off. In the illustrated embodiment, the housing 120 is composed of two sections 120(a), 120(b) that snap together using clips 123.

End cap 125 has a projecting cover 126 that mates with a corresponding cutout in pad side of housing section 120(b) to provide easy access to the defibrillator pads 116 and other components in the drawer compartment when end cap 125 is removed. The end caps 124, 125 may be color coded which helps a user following the instructions for use remove the end cap 124 that covers the compartment that houses connector cable 113 first in order to expedite the process of getting the phone plugged in to begin capacitor charging.

The electronics mount to an internal frame (sometimes referred to as an electronics cage or skeleton), which also serves to help join the two halves of the exterior body together securely. The housed electronics include a high voltage capacitor 209, a low voltage circuit board 237 and high voltage circuit board 238. In the illustrated embodiment, the internal frame includes three longitudinally spaced apart plates, with a plurality of beams extending between the plates to form a PCB cage and a capacitor cage respectively which are illustrated in more detail in the incorporated provisional application No. 62/433,067.

The pad side housing section 120(b) has an internal flange that serves as a stop for the internal frame. More specifically, one of the plates abuts against and is coupled to the flange 127 by appropriate fasteners such as screws (although clips or other fasteners may be used). The connector cable side housing cable has a similar flange 128 to which plate 131 of the internal frame is attached in a similar manner. These structures together with clips 123 hold the electronics cage firmly in place in the assembled product and cooperate with the cage to help protect the defibrillator electronics in the event of rough handling.

Each end cap may have a structure attached thereto that can readily be gripped and pulled by the user to remove the cap when the AED is used. In some of the illustrated embodiments, the pull structure takes the form of a loop integrally molded into the end cap. In another alternative, each end cap may have a straps attached thereto. The free end of each strap has a round tangs that serves as a pull tab that can be pulled by the user to easily remove the respective end caps from the housing 120. In other embodiments, a variety of other grip mechanism can be used to make it easier for a user to remove the end caps.

The housing 120, the end caps 124, 125 and the internal structural skeleton structure may all be fabricated from plastic which works well due to plastic's low electrical conductivity, light weight, and ease of manufacturing. However, it should be appreciated that other appropriate materials may be used for some or all of these components in other embodiments.

In some embodiments, one end of the connector cable 113 is hard wired to the low voltage circuit board 237. However, in other embodiments a connector may be provided to facilitate coupling the connector cable to the defibrillator electronics. The defibrillator pads 116 preferably have connectors that plug into pad connector port 156 that is mounted on the housing 120. This allows the defibrillator pads to be readily exchanged when appropriate, as for example every few years to ensure that the pads are always effective, after a use, or to facilitate the use of training pads during training. Each pad 116 preferably has an associated wire that is long enough to permit the pads to be placed on the patient in either (i) an across the chest configuration or (ii) a front and back configuration, as appropriate when the defibrillator is used. The use of a quick connector also allows the use of different pads for pediatric and adult cardiac events with the user simply plugging in the appropriate pads at the time of use.

Figure 15A:
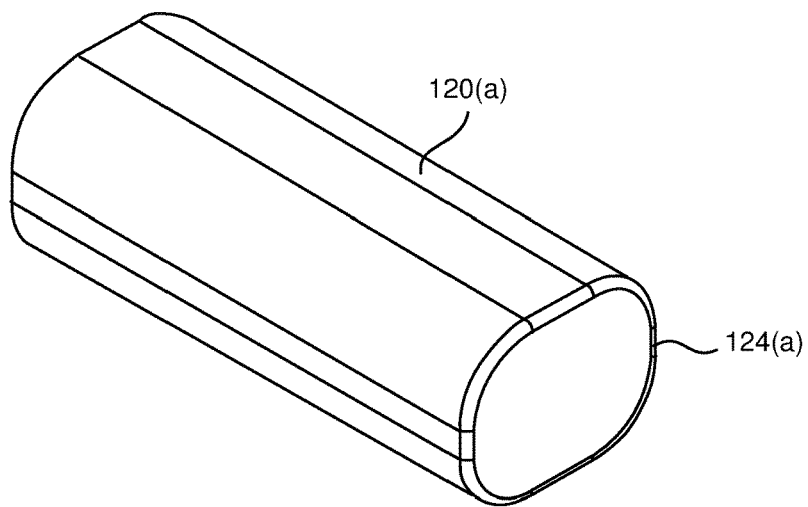
FIG. 15A is a perspective view of an alternative tubular defibrillator housing embodiment that has a single end cap.
Figure 15B:
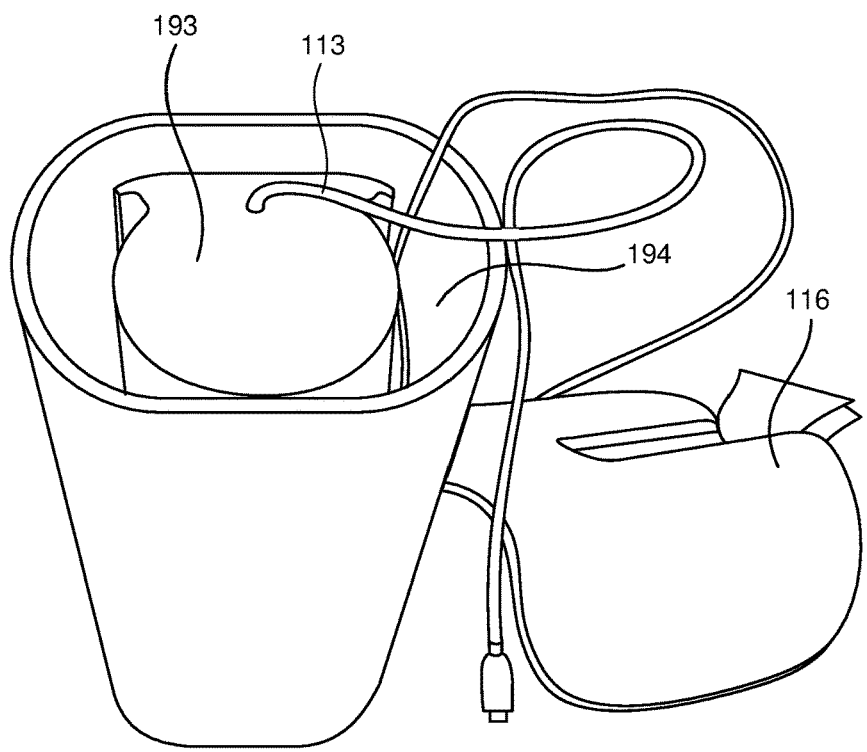
FIG. 15B is an end view of the tubular defibrillator housing illustrated in FIG. 15A.

FIGS. 15A and 15B illustrate another embodiment of an oval-shaped tubular housing 120(a). As best seen in FIG. 15A, housing 120(a) also has a stadium shaped oval cross section with a pair of flat sides, but has only one end cap 124(a). In this embodiment, both the connector cable 113 and the pads 116 are accessible through the end cap 124(a). The end cap 124(a) has a pull feature 129 that may be pulled to separate the end cap from the housing 120(a). In the illustrated embodiment, the pull feature 129 takes the form of a loop. When desired, a pull strap may be attached to the loop. The strap may be pulled to remove the end cap from the end of housing 120(a). In other embodiments, a variety of different pull features may be utilized in place of the described loop/strap arrangement.

The housing 120(a) may be molded as a single piece such that it's only opening is the end covered by end cap 124(a). The end cap 124(a) may be sealed using an o-ring (not shown). Thus, like the previously described embodiment, the exterior of the housing 120(a) is screwless and watertight, allowing the AED to be transported, and if necessary used, in a variety of weather conditions.

FIG. 15B is an end view of the housing 120(a) with the end cap 124(a) removed. In the illustrated embodiment, the interior of housing 120(a) includes a pads compartment 193 that houses the electrode pads 116 and a compartment 194 that houses the defibrillator electronics.

The external appearance of selected embodiments of the defibrillators shown in FIGS. 1 and 14-15 are illustrated U.S. Design Application No. 29/626,141, which is incorporated herein by reference.

In other embodiments a single flat edge or more than two flat edges can be provided. At least one flat edge is often desirable for a tubular housing to prevent rolling and a single flat edge can help orient the defibrillator.

FIGS. 16 and 17 illustrate yet another housing configuration. In this embodiment, defibrillator unit 710 includes a dedicated smart phone 705 that is integrally packaged in housing 720 such that the phone's display screen 706 is exposed and can be used as the display for defibrillator unit 710. As best seen in FIG. 17, the housing 720 includes three compartments 722, 723 and 724. Compartment 722 houses the dedicated smart phone 705. The smart phone has a touch screen display 406 that is exposed through an opening in compartment 722 such that the smart phone can be operated in a generally conventional manner. Compartment 723 houses the electrode pads 116. Compartment 724 houses the defibrillator electronics.

In the embodiment of FIGS. 16-17, the housing 720 has a "gem-shaped" cross-section with several flat sides that the defibrillator can rest on during storage or use. In the illustrated embodiment, the housing has: a front surface 731 that exposes the display screen 706; a back surface 732 that is substantially parallel to the display screen; two upper side surfaces 734, 735 that taper outwardly and downward from opposing sides of the front surface; two lower side surfaces 737, 738 that taper inwardly and downward respectively from the upper side surfaces 734, 735 to the back surface 732. The housing also has end walls 739 on opposing ends of the housing. In the illustrated embodiment, upper side surface 734 includes an opening 741 that provides access to the second compartment 723 to provide access to the electrode pads 116. In some embodiments, the pads opening 741 takes up substantially the entire face of upper side surface 734. In others the opening is smaller relative to the size of the upper side surface 734. In some embodiments the display opening in compartment 722 takes up substantially the entire face or at the vast majority of the face of front surface 731 such that the face of the front surface is only slightly larger than the face of the mobile communication device. In many embodiments the junctions between the various side surfaces are rounded to provide smooth corners. In the illustrated gem shaped embodiment, the defibrillator may be supported for use on any of lower side surfaces 737, 738, back surface 732 or either end surface 739.

In the perspective view of FIG. 16, the phone is shown in place. FIG. 17 shows the housing 720 itself (i.e., empty) such that the three compartments 722, 723 and 724 can be seen. An end cap (not shown in FIG. 17, but in place in FIG. 16) attaches to the open end of the housing 720 to hold the components in place. Like the other embodiments, the housing 720 may be sealed to be water tight. It should be appreciated FIG. 18 illustrates another integrated housing 720(a) that is similar to the embodiment of FIGS. 16 and 17 with a difference being that the housing 720(a) has a rounded bottom 723(a) rather than a flat back surface 732. The other surfaces of housing 720(a) are similar to the front, side and end surfaces described above with respect to FIGS. 16-17. The external appearance of selected embodiments of the defibrillators shown in FIGS. 16-18 are illustrated U.S. Design Application No. 29/626,256, which is incorporated herein by reference.

Although a few specific housing geometries have been shown, it should be appreciated that the described defibrillator electronics can be packaged into a wide variety of different form factors. Conversely, the described housings may be used to package defibrillators having a wide variety of different capabilities.

The App and Process Control

The app 108 is installed, or installable in memory on the mobile communication device 105. Preferably the app is installed on the mobile communication device and the user practices with both the app and the defibrillator before it becomes necessary to actually utilize the defibrillator in a medical emergency. The app can be factory installed on the mobile communication device as part of a health related suite of apps or can be downloaded from an appropriate app store. The app model allows the user interface and phone based control logic to be updated with improvements, including any new ECG interpretation techniques and/or recommended shock treatment practices and protocols. In still other embodiments, the app may be loaded into memory on the defibrillator unit 110 that is accessible by processor 202 such that it can be automatically cross installed onto the phone (or other mobile communication device) when the defibrillator unit is first connected to device 105 if no suitable app already resides on the connected device 105 at the time of use.

The incorporated U.S. Provisional Patent Application Nos. 62/433,067 includes screenshots showing a representative set of instructions screens that may be presented on the display of the mobile device to guide a user through the use of the AED. The instructions are believed to be self-explanatory. Of course the presentation and content of the user instructions and user interfaces may vary significantly and the flow of the presentation may vary based on various status information that becomes available to the app 108 during use of the device.

Preferably any user instructions are also spoken through the phone's speakers in a calm and confident tone in parallel with their display on the display screen. This allows some user to better focus on the tasks at hand rather than reading all instructions from the display screen. It also can help calm the user down during a high stress event.

Figure 13:
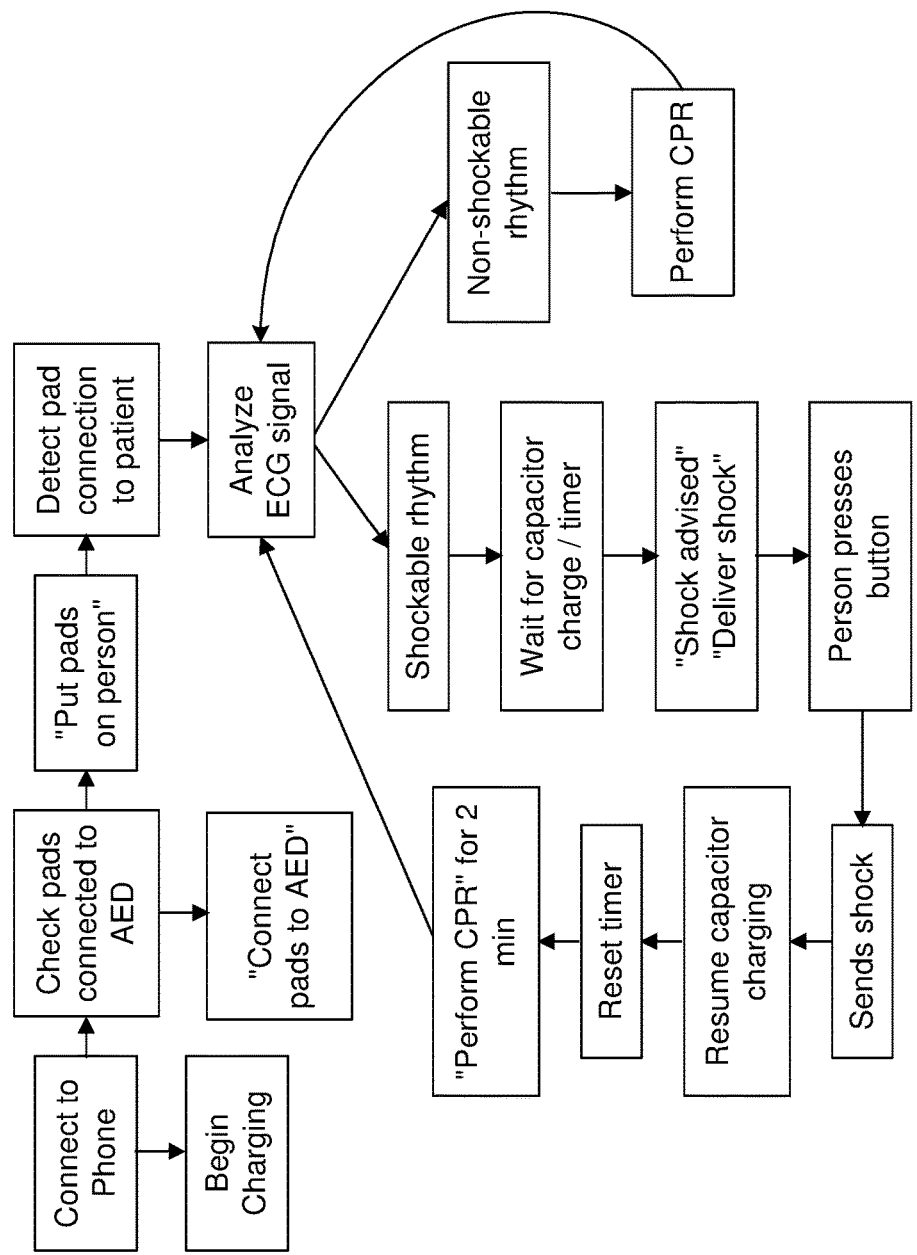
FIG. 13 is a flow diagram illustrating a process flow suitable for controlling the described defibrillators.

In some implementations, much of the control of the AED is performed by the app 108, although it should be appreciated that in different implementations, various aspects of the AED control may be distributed between the app and the on-board controller 202. The overall process control is generally illustrated in FIG. 13.

Initially the defibrillation unit 110 is plugged into the I/O port on phone 105 (or other mobile device) using connector cable 113. When the connection is made, controller 202 is powered, initializes and sends a message to the phone 105 to automatically launch app 108 if it has not already been opened by the user. Alternatively, the user can manually launch the app in a conventional manner at which point the user will be prompted to plug the connector cable 113 from the defibrillation unit 110 into the phone if that hasn't already been done. Preferably both initiation approaches are supported so that the AED picks up immediately from the appropriate point regardless of how the user starts.

As soon as the phone is connected to the defibrillation unit, the capacitor begins to charge with the charging being regulated by current regulating circuit 207. The app also preferably checks to determine the current level that can safely be drawn from the phone's battery for charging. In some embodiments, the app determines and stores the maximum current draw permitted by the device on which is installed at the time of installation. If the permissible current draw is different than the default current draw, the app 108 may instruct the controller 202 to set the current regulating circuit 207 to draw current at the approved level.

In parallel with the capacitor charging, a check is made to determine whether the defibrillator pads 116 have been connected to the AED. If not, the user is instructed to plug the pads 116 into the defibrillation unit. It is noted that the pads wires have connectors that plug into a mating connector 156 on the housing 120. Once the connection of the pads has been verified, the control routine then instructs the user to place the defibrillation pads 116 on the patient. The fact that the pads 116 have been placed on a patient can be automatically detected by monitoring the impedance between the pads which will be lowered when the pads are attached to the patient's skin. Once the pads are attached to the patient, the ECG signals can be analyzed to determine whether the patient's condition is shockable or non-shockable. Any of a variety of publically available or proprietary QRS detection algorithms may be used to determine the nature of the patient's heart rhythms and the appropriate shock voltage/intensity may be determined accordingly. If one of the pads becomes detached from the patient at any time, the user can be warned and instructed to reattach or better attached the pad of concern.

If the cardiac rhythm is determined to be shockable, the control logic determines whether the capacitor is already charged to the desired level. If not, the logic waits for the capacitor to charge to the desired level. The app 108 can poll defibrillator controller 202 to request the current charge or may simply request that the capacitor be charged to a desired level. If asked for the current charge, the defibrillator controller 202 simply returns the current charge level. If asked to charge to at least a designated voltage threshold, the controller 202 monitors the charge state of the capacitor and sends a message to the app once the desired charge is reached. Whether the capacitor keeps charging after the designated threshold is hit depends on whether the threshold identified by the app is a minimum voltage threshold or a maximum voltage threshold. In various embodiments, either the voltage level or the amount of energy stored can be controlled. In embodiments in which the capacitor energy storage amount and voltage level can be controlled somewhat independently, both types of control may be used.

Once it is confirmed that the capacitor has been charged appropriately, the user is informed that a shock is advised and instructed to stand clear of the patient, an initiate shock button is displayed on the mobile phone's screen. When the user presses the button an initiate shock command is sent from the app 108 to defibrillator controller 202, which initiates the shock. As soon as the shock is delivered, capacitor charging resumes and the AED returns to the ECG monitoring mode. The newly received ECG signals are analyzed by the app and the cycle can be repeated as necessary. In parallel, the user may be instructed to perform CPR for a period of time—as for example two minutes. Similarly, if the ECG analysis determines that no shockable rhythm exists, the user may be prompted to perform CPR if CPR is advised.

In some embodiments, the app can be configured to alert the user that it will be delivering a discharge, and then proceed to deliver a discharge without user input after the user has had an opportunity to stand back.

The app may also optionally be configured to automatically contact or call an emergency number (such as 911 or a doctor on call) when it is first deployed to request emergency assistance and/or to provide the first responders with the patient's exact GPS coordinates. The contact can be in any desired form including text based messages, a prerecorded voice message, a live connection or any other suitable form of messaging.

In some implementations the user is given an option to connect directly with a doctor (or other emergency medical personnel) who can help them manage the medical situation. Such a live connection can be in the form of a standard or IP based phone call, a video connection or other appropriate mechanism. If desired, the app can have a button that can be selected by the user to initiate such a connection.

In some embodiments, the app is configured to keep a log of the activities that occur during use. This includes persistently storing a full shock history—which may include information such as: an indication of the number of shocks delivered; the energy delivered in each shock; and the time at which each shock was administered. Other shock related information such as the voltage or waveform utilized in each applied shock, etc. may be provided as well if desired.

The log also records all ECG signals that were received throughout the entire period of use (regardless of whether a shock is applied) and the diagnosis made that lead to the decision regarding whether or not to initiate a shock (e.g., the diagnosed condition is ventricular tachycardia). This event history log will typically be stored locally in the memory of the mobile communications device—although in other embodiments it may additionally or alternatively be stored in memory on the defibrillator or transmitted to a remote server.

The event/shock history is preferably also made available to emergency responders when they first arrive at the scene. In some implementations, an icon or other GUI button (such as an "i" icon—not shown) is displayed on each user interface screen associated with the app that when pushed immediately transitions the screen to an event history screen which shows the medical personnel exactly what has been done with the patient up to that point and can show the first responders/medical personnel the nature of the patient's ECGs both before and after the delivery of any shock(s). This type of immediate access to the shock history can be of great use to the medical personnel in determining what actions to take next. In such embodiments, pressing the icon from an event history or manual operation mode can cause the defibrillator to transition back to its standard AED mode.

Since the shock history is persistently stored, it can also be transferred to or accessed by doctors treating the patients at a later time. Such records can also be useful in studying the efficacy of different shock profiles for treating specific types of cardiac events. It should be appreciated that the shock history is medical information and therefore, if the information is shared outside of the incident itself, any transmission or sharing of such information should be secure and compliant with any applicable medical information handling standards, such as HIPAA in the United States.

In some embodiments, the app can be configured to operate the defibrillator as either an AED or a manual defibrillator. In the manual defibrillator mode, the operator (which should be a trained medical practitioner or first responder) is given more control over the nature of the shock delivery. By way of example, the operator may be allowed to set the amount of energy to be delivered by the shock, the shock voltage and/or other characteristics of the shock waveform. When the app transitions to the manual operation mode, the event history and ECG waveforms are preferably displayed or made available to the user as discussed above.

The app can also be arranged to provide the owner of the AED with important reminders such as alerts notifying users when they need to replace the pads in their mobile phone powered defibrillator (pad for example need to be replaced every few years and failure to replace the pads when advised is a source of AED malfunctions—and breakdowns during use). Having these alerts on the cell phone, a device which people use and check on a regular basis, increases user awareness as to the state of their medical equipment and the kinds of action the user needs to take to keep their defibrillator in good working condition.

These notifications can be delivered to the host mobile device as use notifications (e.g., using the notifications function on Apple and Android devices), and/or as SMS or other suitable messages—which are particularly useful when the notification(s) is/are delivered to other mobile devices. The use of the host device's notification system is particularly powerful when the host device for the app is a registered user/owner's personal device. In embodiments in which a dedicated smart phone or the like is provided as an integrated component of the defibrillator (as for example in the embodiments of FIGS. 16-18), the notifications may additionally or alternatively be sent to the registered owner/user's personal device using SMS or other suitable messaging technologies. In still other embodiments, a message can be sent to an intermediary remote server (or a functional equivalent) and then sent from that remote server to a registered user's personal device.

There are a wide variety of notifications that may be provided. For example, low battery notifications may be provided. In the context of a personal phone, the app can also be aware of the host mobile device's battery charge level such that it can alert the user when the battery is below recommended AED-Operating levels. In the context of embedded phone defibrillators, the notification can be that it is time to recharge the battery for the AED. In some embodiments, multiple level notifications can be sent. For example, a first notification can be transmitted when a charge is recommended and a second notification can be sent when the battery is critically low.

In many embodiments, the defibrillator is configured to periodically execute self-checks to make sure that it is still in good operating condition. In other embodiments, the app may be configured to direct the execution of such tests. Alert notifications may be used to inform the owner that a self-test has failed or that the defibrillator requires attention or that it is time to plug the user's phone into the defibrillator in order to test the defibrillator.

Another example of an alert that can be provided is a reminder to take a refresher course when a User's CPR certification has expired.

A variety of incident alerts may also be sent in the event that the defibrillator is deployed. The incident alerts may be sent via SMS messages or using any other suitable messaging protocol. These incident alerts may be sent automatically in response to the user pushing an "emergency" button displayed on the user interface. The app may be configured to prompt a user to push the emergency button if the device is being deployed in a real emergency. In some embodiments, an incident alert may be automatically sent to an emergency number (e.g., 911 in the United States) to initiate alerting first responders. The incident alert may provide the recipient with a variety of different information, including the nature of the event (e.g., a potential cardiac arrest), and the location of the event (etc.)

In some embodiments, an incident alert may be sent automatically to one or more of a registered owner of the defibrillator, a person responsible for the defibrillator and/or any other person that may have reason to know that an incident is in progress. This type of alert is especially useful when the defibrillator is kept in a public location—as for example at a school, at a sports field, or in any other public space. In one particular example, if a school has a nurse or a teacher or administrator that is trained on use of the defibrillator, such person can immediately be informed of the existence and location of an emergency on school premises so that they can immediately respond to the event.

The app may also provide CPR instructions for an inexperienced user of the AED who doesn't know, or can use a refresher on CPR. Furthermore, using analysis algorithms on the phone, it is possible to estimate whether or not CPR was performed on the patient, which is information that can be presented to the EMTs upon their arrival.

Inductive Charging

In many of the embodiments described above, a connector cable or other wired connection is utilized to connect the defibrillator unit to the mobile device. However, in other embodiments the connection can be entirely wireless. For example, it is likely that wireless charging will become a common feature in smart phones and other mobile communication devices in the near future. When a mobile device is configured to support wireless inductive charging, it can readily be adapted to deliver energy to peripheral devices using the same coils and circuitry. The defibrillator can readily be adapted to receive its discharge capacitor charging power through a wireless charging interface. By way of example, one such embodiment is illustrated in FIG. 20.

Figure 20:
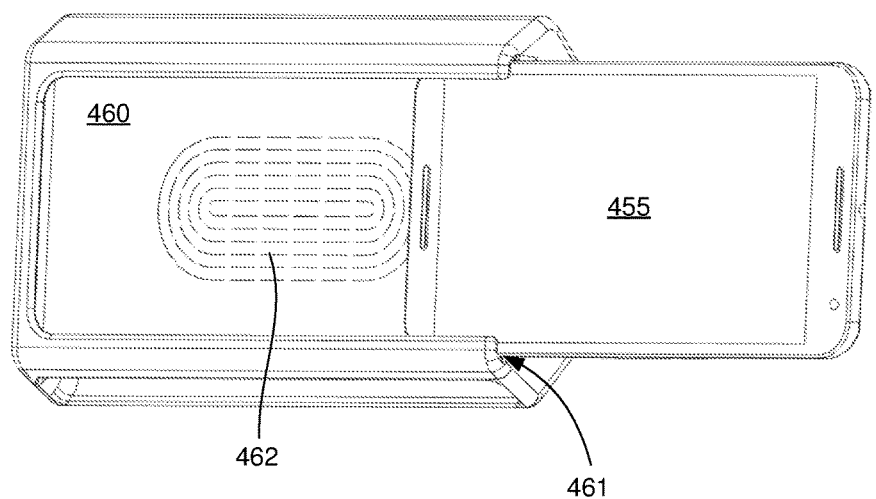
FIG. 20 is a perspective view of a defibrillator that utilizes inductive charging to delivery electrical energy to the charging circuit.
Figure 9:
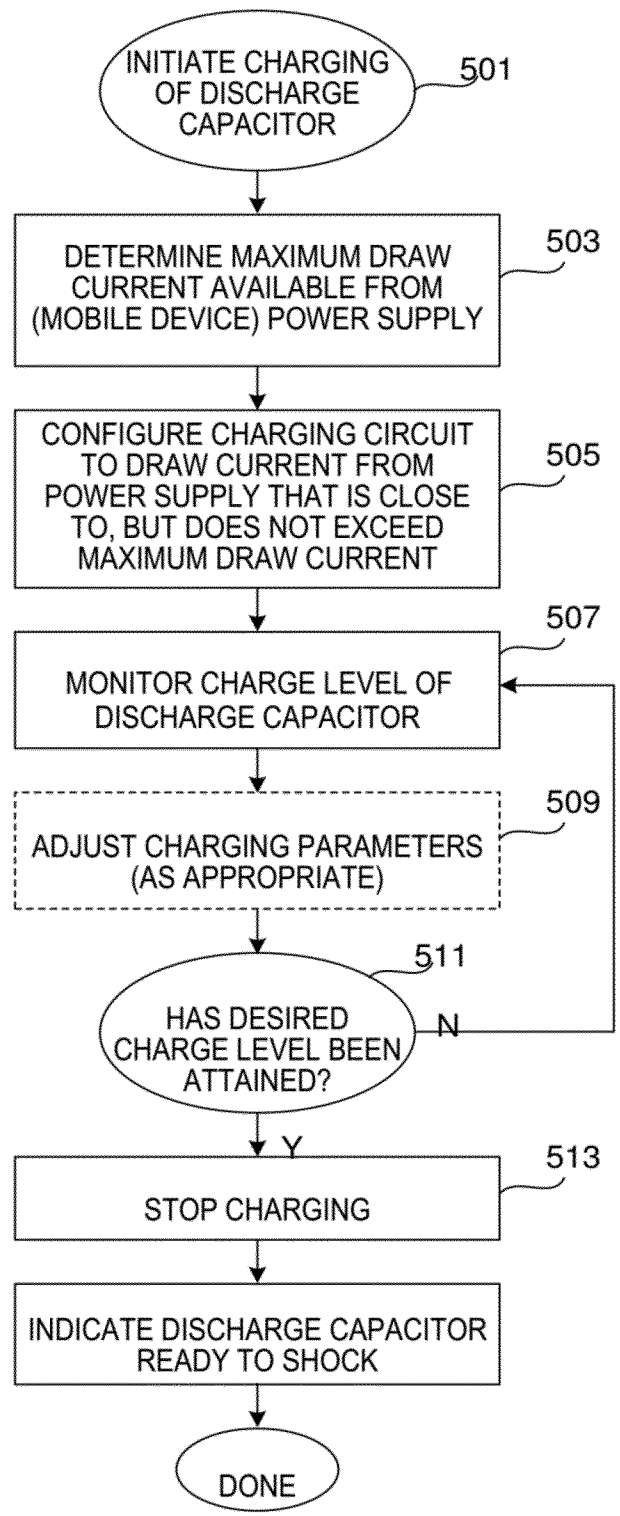

In the embodiment of FIG. 20, the defibrillator housing 460 includes a mobile device receptor 461 that is configured to receives a smart phone 455 having an inductive charging coil (not shown) near its back surface. The housing also includes an inductive charging coil 462 that is positioned adjacent the location that the smart phone charging coil would be located when placed in the receptor 461. With this arrangement, the energy for the discharge capacitor charging circuit can readily be supplied through inductive charging from the smart phone 455 or any other suitable mobile communication device that supports inductive charging.

Other Embodiments

Although only a few embodiments of the invention have been described in detail, it should be appreciated that the invention may be implemented in many other forms without departing from the spirit or scope of the invention. For example, although particular logic and electronic circuitry has been described to facilitate explanation of various aspects of the invention, it should be appreciated that the actual electronic circuits, algorithms and/or logic used to accomplish the described functions may vary widely and are in no way intended to be limited to the accompanying diagrams, figures and flow charts. Rather, various components, steps and functions may be reordered, altered, added or deleted in accordance with designer preferences and/or the needs of any particular implementation.

The use of ubiquitous mobile devices such as smart phones and tablet computers as a power supply has the potential to facilitate reductions in the size and cost of the described defibrillators relative to various commercially available defibrillator designs as well as to reduce some of the shelf life concerns of many traditional AEDs. The use of the app 108 as part of the defibrillator control also allows the defibrillator designer to take advantage of the powerful processing power of smart phones in the analysis of the heart rhythms. The flexibility afforded by using an app to control the defibrillator also allows the ECG signal processing and defibrillator control logic to be readily updated to reflect the latest developments in cardiac care.

The use of a smart phone based app as the user interface also has an important advantage of familiarity to the user. That is, since most users interact with apps on their phone every day, packaging the user interface in an app makes people feel more comfortable when responding to an emergency situation that requires use of an AED.

The app can also be configured to provide metrics related to the defibrillators' use. This data can further be used to infer about general AED performance, perform studies on people's reaction to emergency situation, and ultimately inform redesigns of the product.

The various control methods described herein can be implemented using software or firmware executed the defibrillator controller, an app executed on a smartphone or other mobile computing device and/or any other processor suitably programmed with appropriate control algorithms. Alternatively, when desired, the functionality can be implemented in the form of programmable logic (e.g. programmable logic arrays, FPGAs, etc.) or using application specific integrated circuits (ASICs) or a combination of any of the foregoing.

When software or firmware algorithms are used, such algorithms may be stored in a suitable computer readable medium in the form of executable computer code(programmed instructions) with the operations being carried out when a processor executes the computer code. The defibrillator or the defibrillator controller may include memory suitable for storing all of the code that is to be executed by the defibrillator and the mobile device includes memory suitable for storing the defibrillator app and/or other software or firmware to be executed by the mobile device.

The defibrillator may also be used for training purposes. When used for training, the capacitor is not charged upon connection with the phone (this can be accomplished by sending a command from phone to the controller 202 instructing the controller 202 not to charge). In this mode the AED itself can be used in simulated emergency scenario for practice without the user risking inadvertent discharge of the defibrillator. During such practice, the user can practice attaching pads, performing CPR, and practice responding to an emergency cardiac arrest situation.

In the primary described embodiments, the defibrillator capacitor 209 is charged from the phone when the AED is deployed. Although this is expected to be a common use scenario, other use scenarios can be supported as well. For example, if the user will be attending a particular event at which they are particularly concerned about the risk of someone having a heart-attack, they could proactively charge the AED prior to the event. To support such a usage model, the AED can be configured to charge passively dissipates the capacitor charge over several days rather than over a shorter period of several hours or less which would may optionally be provided in order to reduce the risk of an shock being inadvertently delivered.

In another use scenario, the defibrillator can include a small battery which serves as a supplementary power supply. The availability of this type of supplementary power ensures that the AED can be used even if the phone is nearly fully discharged. At the same time, the phone provides an additional power supply in the event that more shocks are required than can be supported by the supplementary power supply. The supplementary power supply may be housed in a wide variety of locations within the device such as in one of the compartments exposed by the end caps. In one particular implementation, a modular battery pack can be provided that fits into the connector cable compartment of housing 120. The module can optionally be arranged such that the phone cable can be pulled through a center section in this modular battery pack, and repackaged on the outer side of this module. This module can further be arranged to have all the necessary control system on it to turn the AED into a self contained device that can operate without the phone if necessary. For example, the module can include the ECG processing logic, speakers for user interface, and a manual shock button for the user push. It should be appreciated that because the supplementary battery's discharge rate (and the corresponding charge time) can be controlled, the supplemental battery does not have to be as large as the batteries provided with most AEDs.

More generally, the described mechanical design allows for modular components to be readily added at the ends and integrated with the main defibrillator circuitry and mechanical design. One such potential add-on is the supplemental battery described above. However in other embodiments any other suitable modules could be added, including for example a first aid supply module or compartment, etc.

Many conventional portable AEDs are placed in cabinets at public or private locations so that they are available in the event of an emergency. Thus, in practice they tend to sit unused for extended periods of time (potentially multiple years) and they are expected to perform well when needed. A problem that is sometimes encountered is that when it comes time to use a conventional AED, its battery may have discharged to a level that makes the AED unusable or less functional than desired. Such problems can be mitigated by providing such AEDs with one or more connectors that allows the AED to be coupled to a phone, tablet or other mobile communication device and supplemental capacitor charging circuitry as described herein (e.g., a controller, current regulating circuitry and voltage booster) to allow supplemental power to be supplied to the AED from the phone as necessary. In still other implementations, conventional AEDs can be adapted to interface with the described app (either through a connector cable or wirelessly) to provide a better user interface when the device is used. ECG data and shock protocols utilized may also be uploaded to the phone for presentation or transmission to trained medical personnel (e.g. first responders, emergency room personnel, treating doctors, etc.).

The embodiments describe above focus primarily on defibrillators that are intended for use with a mobile communication device. The mobile devices may be personal (e.g., off the shelf) cell phones, tablet computers, etc., or in some embodiments may be packaged together with the defibrillator. In still other embodiments, many of the described features including the charging circuits, the dynamic discharge impedance detection, the discharge circuits, the housing form factors, etc. may be used in the context of more conventional defibrillators that do not require the availability of a mobile communication device in order to operate.

Most of the described embodiments include one or more shock discharge capacitor(s) that is/are individually or together capable of delivering a defibrillation shock to a patient. In general, any of the described capacitors may be thought of as a capacitor unit having one or more individual capacitors that is/are configured appropriately to accomplish the desired task. When more than one physical capacitor is utilized in a capacitor unit, such capacitors may be connected in series and/or parallel and/or in any other appropriate manner to perform the desired functionality.

Several of the described embodiments contemplate the use of a transitory electrical energy store that helps maintain a continuous draw of current from a power supply when a voltage boosting element such as a transformer draws current in periodic intervals (i.e., oscillates between current shut-off and current draw states). The transitory electrical energy store temporarily stores electrical energy store drawn from a power supply when current to the voltage booster during the current shut-off intervals, and supplies that additional current to the voltage booster during the current draw intervals. It should be appreciated that the transitory electrical energy store can also be used in voltage boosting designs that cycle between high and low current draw rates.

Although the described form factor provide compact designs making the defibrillator itself highly portable and easy to use, it should be appreciated that a variety of different form factors may be used in alternative embodiments. Similarly, although specific electronic circuits, defibrillator control logic and user interfaces have been described, it should be appreciated that all of these features may be widely varied. Therefore, the present embodiments should be considered illustrative and not restrictive and the invention is not to be limited to the details given herein, but may be modified within the scope and equivalents of the appended claims.

The invention claimed is:

1. A defibrillator comprising:
    a capacitor unit configured to store and discharge sufficient energy to deliver a defibrillation shock to a patient;
    voltage boosting circuitry configured to boost the voltage of received current to charge the capacitor unit to a voltage suitable for delivery of the defibrillation shock, wherein during charging the voltage boosting circuit cyclically draws current during periodic current draw intervals and does not draw current during intervening current shut-off intervals; and
    current regulating circuitry configured to maintain a continuous current draw from a power source for the voltage boosting circuitry throughout the charging of the capacitor unit, the current regulating circuitry including a transitory electrical energy store that serves as a temporary store for electrical energy drawn from a power source during the voltage boosting circuitry's current shut-off intervals and as a supply of supplemental current to the voltage boosting circuitry during at least portions of the periodic current draw intervals.

2. A defibrillator as recited in claim 1 wherein the voltage boosting circuitry includes a flyback converter.

3. A defibrillator as recited in claim 1 wherein the voltage boosting circuitry has an input voltage of no more than approximately 5 volts and an output and is configured to charge the capacitor unit to a voltage suitable for delivering the defibrillation shock.

4. A defibrillator as recited in claim 1 wherein the transitory electrical energy store has a variable electrical characteristic that may be changed during charging of the capacitor unit.

5. A defibrillator as recited in claim 4 wherein the variable electrical characteristic of the transitory electrical energy store is selected from the group consisting of: variable capacitance, variable inductance; and both variable capacitance and variable inductance.

6. A defibrillator as recited in claim 5 wherein the variable electrical characteristic of the transitory electrical energy store is set by a defibrillator controller based at least in part on a current voltage of the capacitor unit.

7. A defibrillator as recited in claim 1 wherein the transitory electrical energy store includes a plurality of capacitors arranged in parallel, the capacitors in the transitory electrical energy store having different capacitances.

8. A defibrillator as recited in claim 1 wherein the transitory electrical energy store includes:
    at least one inductor; or
    at least one capacitor and at least one inductor.

9. A defibrillator as recited in claim 1 wherein the power source is a mobile communication device.

10. A defibrillator as recited in claim 9 further comprising a defibrillator housing, wherein the housing holds the mobile communication device, the capacitor unit, the voltage boosting circuitry and the current regulating circuitry in an integrated package.

11. A defibrillator as recited in claim 9 wherein the mobile communication device is not a part of, integrated with, or coupled to the defibrillator in any way during normal use of the mobile communication device.

12. A defibrillator as recited in claim 1 wherein the current regulating circuitry further comprises:
    a current sensor for sensing the current drawn from the power source; and
    a controller that receives a sensed input current from the current sensor and turns an input switch of the voltage boosting circuitry on and off to maintain the current drawn from the power source within a designated range.

13. A defibrillator as recited in claim 12 wherein the controller is programmable to define the designated range.

14. A defibrillator as recited in claim 1 wherein the defibrillator is arranged to draw current from more than one power source to feed the voltage boosting circuitry, wherein a first one of the power sources is from a device that is external to the defibrillator and a second one of the power sources is a component of the defibrillator.

15. A defibrillator comprising:
    a capacitor unit configured to store and discharge sufficient energy to deliver a defibrillation shock to a patient;
    voltage boosting circuitry configured to boost the voltage of received current to charge the capacitor unit to a voltage suitable for delivery of the defibrillation shock wherein the voltage boosting circuitry includes a transformer having a primary coil; and
    current regulating circuitry configured to regulate a current draw from a power source for the voltage boosting circuitry throughout the charging of the capacitor unit, the current regulating circuitry being configured such that a maximum current through the primary coil may be programmably set during charging of the capacitor unit.

16. A defibrillator as recited in claim 15 further comprising a defibrillator controller, wherein the voltage boosting circuitry includes a flyback converter that includes the transformer having the primary coil, the flyback converter being configured such that a maximum current through the primary coil may be set and reset by the defibrillator controller during charging of the capacitor unit to help maintain the current draw from the power source at a level that is near, but does not exceed a designated power source current draw, the maximum current through the primary coil being higher than the designated power source current draw.

17. A defibrillator comprising:
a capacitor unit configured to store and discharge sufficient energy to deliver a defibrillation shock to a patient;
voltage boosting circuitry configured to boost the voltage of received current to charge the capacitor unit to a voltage suitable for delivery of the defibrillation shock;
current regulating circuitry configured to regulate a current draw from a power source for the voltage boosting circuitry throughout the charging of the capacitor unit; and
a defibrillator controller wherein at least one of the current regulating circuitry and the voltage boosting circuitry is programmable by the defibrillator controller to control the level of current drawn from the power source.

18. A defibrillator as recited in claim 17 wherein the defibrillator controller is configured to maintain the current draw from the power source within a designated range throughout the charging of the capacitor unit.

19. A defibrillator as recited in claim 17 wherein:
the power source is a mobile communication device; and
the defibrillator controller is arranged to communicate with the mobile communication device and to control the level of current drawn from the mobile communication device based at least in part on a current delivery capability of the mobile communication device to which the defibrillator is attached.

20. A defibrillator as recited in claim 19 wherein the defibrillator controller is configured to receive a maximum draw current parameter from the mobile communication device and to program the current regulating circuitry's maximum input draw current based at least in part on the received maximum draw current parameter.

21. A method of charging a defibrillator discharge capacitor, the method comprising:
charging the defibrillator discharge capacitor using a voltage boosting circuit that, during charging, cyclically draws current during periodic current draw intervals and does not draw current during intervening current shut-off intervals; and
maintaining a continuous current draw from a power source for the voltage boosting circuit using a transitory electrical energy store that serves as a temporary store for electrical energy drawn from a power source during the voltage boosting circuitry's current shut-off intervals and as a supply of supplemental current to the voltage boosting circuitry during at least portions of the periodic current draw intervals.

22. A method as recited in claim 21 wherein the transitory electrical energy store has a variable electrical characteristic that may be changed during charging of the capacitor unit and wherein the variable electrical characteristic of the transitory electrical energy store is selected from the group consisting of (a) variable capacitance, (b) variable inductance, and (c) both variable capacitance and variable inductance, the method further comprising resetting the variable electrical characteristic during the charging of the defibrillator discharge capacitor based at least in part on a then present voltage or charge level of the defibrillator discharge capacitor.

23. A method as recited in claim 21 wherein defibrillator further includes a current sensor for sensing the current drawn from the power source, the method further comprising:
turning an input switch of the voltage boosting circuitry on and off to maintain the current drawn from the power source within a designated range.

24. A method as recited in claim 21 wherein the defibrillator includes a defibrillator controller and a charging circuit that includes the voltage boosting circuit, the method further comprising using the defibrillator controller to set or actively control a component of the charging circuit to maintain the current draw from the power source within a designated range throughout the charging of the capacitor unit.

25. A method as recited in claim 24 further comprising changing an electrical characteristic of the charging circuit during the course of a charging cycle to help maintain the current draw from the power source within the designated range.

26. A method of charging a defibrillator discharge capacitor, the method comprising:
charging the defibrillator discharge capacitor using a voltage boosting circuitry that draws current during periodic current draw intervals and does not draw current during intervening current shut-off intervals wherein the voltage boosting circuitry includes a transformer having a primary coil; and
setting a maximum current through the primary coil at the time of charging based at least in part on a current delivery capability of the power supply.

27. A method as recited in claim 26 further comprising changing the maximum current through the primary coil during the charging of the defibrillator discharge capacitor based at least in part on a then present voltage or charge level of the defibrillator discharge capacitor.

28. A method of charging a defibrillator discharge capacitor of a defibrillator using a mobile communication device as the power source, the defibrillator further including a defibrillator controller, a voltage boosting circuit and a current regulating circuit that regulates current supplied to the voltage boosting circuit from the mobile communication device, the method comprising:
determining a current delivery capability of the mobile communication device;
setting a maximum input draw current for the current regulating circuit based at least in part on the determined current delivery capability of the mobile communication device; and
charging the defibrillator discharge capacitor without exceeding the maximum input draw current for the current regulating circuit.

* * * * *

UNITED STATES PATENT AND TRADEMARK OFFICE
CERTIFICATE OF CORRECTION

Page 1 of 2

PATENT NO. : 10,029,109 B2
APPLICATION NO. : 15/834835
DATED : July 24, 2018
INVENTOR(S) : Beyer et al.

It is certified that error appears in the above-identified patent and that said Letters Patent is hereby corrected as shown below:

In the Drawings

Please replace FIG. 9 with FIG. 9 as shown on the attached page.

In the Specification

1. Column 13, Line 49, delete the second occurrence of the word "that".

2. Column 13, Line 63, insert "($t_{dead}$)" after "dead time".

3. Column 13, Line 64, delete "($t_{dead}$)".

4. Column 14, Line 2, change "(out" to --out--.

5. Column 26, Line 24, change "a the" to --as the--.

6. Column 26, Line 64, insert --.-- after "modeled".

7. Column 28, Line 30, insert --.-- after "command".

8. Column 34, Lines 7 and 8, delete "It should be appreciated".

9. Column 38, Line 17, change "event (etc.)" to --event, etc.--.

Signed and Sealed this
Third Day of September, 2019

Andrei Iancu
*Director of the United States Patent and Trademark Office*